United States Patent [19]
Gruber et al.

[11] Patent Number: 5,665,474
[45] Date of Patent: *Sep. 9, 1997

[54] PAPER HAVING A MELT-STABLE LACTIDE POLYMER COATING AND PROCESS FOR MANUFACTURE THEREOF

[75] Inventors: Patrick Richard Gruber, St. Paul; Jeffrey John Kolstad, Wayzata; Christopher M. Ryan, Dayton; Eric Stanley Hall, Crystal; Robin Sue Eichen Conn, Minneapolis, all of Minn.

[73] Assignee: Cargill, Incorporated, Minneapolis, Minn.

[*] Notice: The term of this patent shall not extend beyond the expiration date of Pat. No. 5,475,080.

[21] Appl. No.: 521,923

[22] Filed: Aug. 31, 1995

Related U.S. Application Data

[63] Continuation of Ser. No. 34,099, Mar. 22, 1993, Pat. No. 5,475,080, which is a continuation-in-part of Ser. No. 955,690, Oct. 2, 1992, Pat. No. 5,338,822.

[51] Int. Cl.⁶ ............................ B32B 27/10; B05D 3/02; C08G 63/08
[52] U.S. Cl. ............................ 428/481; 427/391; 428/480; 428/490; 428/537.5; 525/413; 525/415; 528/354; 528/361
[58] Field of Search ............................ 427/391; 428/480, 428/481, 490, 537.5; 525/413, 415; 528/354, 361

[56] References Cited

U.S. PATENT DOCUMENTS

| 1,095,205 | 5/1914 | Grūter et al. | 528/361 |
|---|---|---|---|
| 1,849,107 | 3/1932 | Moss | 528/354 |
| 1,995,970 | 3/1935 | Dorough | 528/354 |
| 2,396,994 | 3/1946 | Filachione et al. | 528/354 |

(List continued on next page.)

FOREIGN PATENT DOCUMENTS

| 863673 | 2/1971 | Canada . |
| 923245 | 3/1973 | Canada . |
| 0107591 | 2/1984 | European Pat. Off. . |
| 0299730 | 1/1989 | European Pat. Off. . |
| 0314245 | 5/1989 | European Pat. Off. . |
| 0052510 | 3/1992 | European Pat. Off. . |
| 0481732 | 4/1992 | European Pat. Off. . |
| 0507554 | 10/1992 | European Pat. Off. . |
| 0510998 | 10/1992 | European Pat. Off. . |

(List continued on next page.)

OTHER PUBLICATIONS

T.M. Jackanicz, *Polylactide Acid as a Biodegradable Carrier for Contraceptive Steroids*, Contraception, vol. 8, No. 3, 227–234 (1973).

A.D. Schwope et al., *Lactic/Glycolic Acid Polymers as Narcotic Antagonist Delivery Systems*, Life Sciences, vol. 17, 1877–1886 (1975).

L.C. Anderson, *An Injectable Sustained Release Fertility Control System*, Contraception, vol. 13. No. 3, 375–384 (1976).

W. Carothers et al., *Studies of Polymerization and Ring Formation. X. The Reversible Polymerization of Six–Membered Cyclic Esters*, 1932. American Chem. Soc. Journal, v. 54, pp. 761–772.

(List continued on next page.)

*Primary Examiner*—Shelley A. Dodson
*Attorney, Agent, or Firm*—Merchant, Gould, Smith, Edell, Welter & Schmidt, P.A.

[57] ABSTRACT

A lactide polymer coating resulting in a strong, repulpable, high gloss, paper coating. The lactide polymer comprises a plurality of poly(lactide) polymer chains, residual lactide in concentration of less than about 5 percent and water in concentration of less than about 2000 parts-per-million. A process for coating paper with the lactide polymer composition is also disclosed.

26 Claims, 2 Drawing Sheets

U.S. PATENT DOCUMENTS

| | | | |
|---|---|---|---|
| 2,703,316 | 3/1955 | Schneider | 528/357 |
| 2,758,987 | 8/1956 | Salzberg | 528/354 |
| 2,951,828 | 9/1960 | Zeile et al. | 528/354 |
| 3,268,487 | 8/1966 | Klootwijk | 528/357 |
| 3,332,791 | 7/1967 | Selman | 549/274 |
| 3,531,561 | 9/1970 | Trehu | 264/210 |
| 3,636,956 | 1/1972 | Schneider | 128/335.5 |
| 3,772,420 | 11/1973 | Glick et al. | 264/102 |
| 3,773,919 | 11/1973 | Boswell et al. | 424/19 |
| 3,839,297 | 10/1974 | Wassermann et al. | |
| 3,887,699 | 6/1975 | Yolles | 424/19 |
| 3,912,692 | 10/1975 | Casey et al. | 528/354 |
| 4,045,418 | 8/1977 | Sinclair | |
| 4,249,531 | 2/1981 | Heller et al. | 128/260 |
| 4,273,920 | 6/1981 | Nevin | 528/361 |
| 4,279,249 | 7/1981 | Vert et al. | 128/92 |
| 4,595,713 | 6/1986 | St. John | 523/105 |
| 4,643,734 | 2/1987 | Lin | 623/16 |
| 4,677,191 | 6/1987 | Tanaka et al. | 528/361 |
| 4,683,288 | 7/1987 | Tanaka et al. | 528/361 |
| 4,719,246 | 1/1988 | Murdoch et al. | 521/134 |
| 4,727,163 | 2/1988 | Bellis | 549/274 |
| 4,728,721 | 3/1988 | Yamamoto et al. | 528/361 |
| 4,766,182 | 8/1988 | Murdoch et al. | 525/413 |
| 4,789,726 | 12/1988 | Hutchinson | 528/354 |
| 4,797,468 | 1/1989 | DeVries | 528/254 |
| 4,800,219 | 1/1989 | Murdoch et al. | 525/413 |
| 4,835,293 | 5/1989 | Bhatia | 549/274 |
| 4,902,515 | 2/1990 | Loomis et al. | 424/486 |
| 4,950,258 | 8/1990 | Kawai et al. | 604/281 |
| 4,960,866 | 10/1990 | Bendix et al. | 528/499 |
| 4,981,696 | 1/1991 | Loomis et al. | 424/486 |
| 4,983,745 | 1/1991 | Muller et al. | 549/274 |
| 4,990,222 | 2/1991 | Aigner et al. | 203/91 |
| 5,011,946 | 4/1991 | Hess et al. | 549/274 |
| 5,023,349 | 6/1991 | Bhatia | 549/274 |
| 5,023,350 | 6/1991 | Bhatia | 549/274 |
| 5,041,529 | 8/1991 | Shinoda et al. | 528/354 |
| 5,043,458 | 8/1991 | Bhatia | 549/274 |
| 5,053,485 | 10/1991 | Nieuwenhuis et al. | 528/354 |
| 5,053,522 | 10/1991 | Muller | 549/274 |
| 5,076,983 | 12/1991 | Loomis et al. | 264/101 |
| 5,097,005 | 3/1992 | Tietz | 528/272 |
| 5,108,399 | 4/1992 | Eitenmuller et al. | 606/77 |
| 5,132,397 | 7/1992 | DeGuia | 528/354 |
| 5,134,171 | 7/1992 | Hammel et al. | 521/98 |
| 5,136,017 | 8/1992 | Kharas et al. | 528/354 |
| 5,142,023 | 8/1992 | Gruber et al. | 528/354 |
| 5,149,833 | 9/1992 | Hess et al. | 549/274 |
| 5,180,765 | 1/1993 | Sinclair | 524/306 |
| 5,216,050 | 6/1993 | Sinclair | 524/108 |
| 5,252,642 | 10/1993 | Sinclair et al. | 524/108 |
| 5,296,282 | 3/1994 | Evers | 428/195 |
| 5,338,822 | 8/1994 | Gruber et al. | 528/354 |
| 5,424,346 | 6/1995 | Sinclair | 524/108 |
| 5,434,004 | 7/1995 | Ajioka et al. | 428/411.1 |
| 5,444,113 | 8/1995 | Sinclair | 524/306 |
| 5,475,080 | 12/1995 | Gruber et al. | 528/354 |

FOREIGN PATENT DOCUMENTS

| | | |
|---|---|---|
| 0515203 | 11/1992 | European Pat. Off. |
| 0532154 | 3/1993 | European Pat. Off. |
| 0533314 | 3/1993 | European Pat. Off. |
| 267826 | 12/1913 | Germany |
| 1083275 | 12/1960 | Germany |
| OS3632103 | 3/1988 | Germany |
| 4-283227 | 3/1992 | Japan |
| 1351409 | 5/1974 | United Kingdom |
| 2145422 | 3/1985 | United Kingdom |
| WO90/01521 | 2/1990 | WIPO |
| WO9102015 | 2/1991 | WIPO |
| WO91/06601 | 5/1991 | WIPO |
| WO91/13207 | 9/1991 | WIPO |
| WO92/00292 | 1/1992 | WIPO |
| WO92/00974 | 1/1992 | WIPO |
| WO92/04410 | 3/1992 | WIPO |
| WO92/04412 | 3/1992 | WIPO |
| WO92/04413 | 3/1992 | WIPO |
| WO92/05167 | 4/1992 | WIPO |
| WO92/05168 | 4/1992 | WIPO |
| WO92/15340 | 9/1992 | WIPO |
| WO91/17155 | 11/1992 | WIPO |
| WO93/02075 | 2/1993 | WIPO |

OTHER PUBLICATIONS

E. Filachione et al., *Lactic Acid Derivatives as Plasticizers Esters of Polymeric Lactic Acid*, 1951, Bur. Agric. Ind. Chem., v. 11, pp. 1–11.

D. Deane and E. Hammond, *Coagulation of Milk for Cheese–Making by Ester Hydrolysis*, 1960, Journal of Diary Science, v. 43, pp. 1421–1429.

Kulkarni et al. ("Biodegradable Poly(lactic acid) Polymers", 1971, *J. Biomed. Mater. Res.*, v. 5, pp. 1 169–181).

A. Schindler, R. Jeffcoat, G. Kimmel, C. Pitt, M. Wall and R. Zweidinnger ("Biodegradable Polymers for Sustained Drug Delivery", 1977, *Contemporary Topics in Polymer Science*, v. 2, pp. 251–287).

I. Luderwald ("Thermal Degradation of Polyesters in the Mass Spectrometer", 1979, *Dev. Polymer Degradation*, v. 2, pp. 77–98).

M. Vert and F. Chabot ("Stereoregular Bioresorbable Polyesters for Orthopaedic Surgery", 1981, *Makromol. Chem.*, Supp. 5, pp. 30–41).

M. Gupta and F.V. Deshmukh ("Thermal Oxidative Degradation of Poly–lactic Acid; Part I: Activation Energy of Thermal Degradation in Air", 1982, *Colloid & Polymer Science*, v. 260, pp. 308–311).

M. Gupta and V. Deshmukh ("Thermal Oxidative Degradation of Poly–lactic Acid; Part II: Molecular Weight and Electronic Spectra During Isothermal Heating", 1982, *Colloid & Polymer Science*, v. 260, pp. 514–517).

D.L. Wise et al., "Sustained Release of an Antimalerial Drug Using a Copolymer of Glycolic/Lactic Acide", *Life Sciences*, vol. 19, 867–874 (1976).

R.A. Miller et al., "Degradation Rates of Resorbable Implants (Polylactates and Polyglycolates): Rate Modification with Changes in Pla/Pga Copolymer Rations", *J. Biomed. Mater. Res.*, vol. 11, 711–719 (1977).

D.K. Gilding et al., "Biodegradable Polymers for Use in Surgery—Polyglycolic/Polylactic Acid Homo and Copolymers": 1. *Polymer*, vol. 2, 1459–1464 (1979).

D.K. Gilding, "Degradation of Polymers: Mechanisms and Implaications for Biomedical Applications", *Biocompatibility of Clinical Implant Materials*, D.F. Williams, ed., vol. 1, 43–65 (1981).

A.M. Reed and D.K. Gilding, "Biodegradable Polymers for Use in Surgery Polyglycolic/Polylactic Acid Homo and Copolymers: 2. In Vitro Degradation", *Polymer*, vol. 22, No. 4, 494–498 (1981).

D.K. Gilding, "Biodegradable Polymers", *Biocompatibility of Clinical Implant Materials*, D.F. Williams, ed., vol. 2, 209–232 (1981).

J.D. Strobel, "Biodegradable Polymers", paper presented at Medical textiles and Biomedical Polymers and Materials Conference held at Clemson, S.C., U.S.A., Dec. 5–6, 1989, Stolle Research and Development Corp., PD 712–01, pp. 1–32 and Attachments A1–A21.

"Biocompatible Composite Would Be Completely Absorbed in the Body", *Advanced Materials*, vol. 12, No. 15, Aug. 1990, p. 6.

"Polylaactides Exhibit Degradability", *Tappi Journal*, Sep. 1991, p. 42.

G. Van Hummel and S. Harkema ("Structure of 3,6–Dimethyl–1,4–Dioxane–2,5–Dione [D–, D–{L–,L–}Lactide]", 1982, *Acta. Crystallogr.*, v. B38, pp. 1679–1681).

F. Chabot, M. Vert, S. Chapelle and P. Granger ("Configurational Structures of Lactic Acid Stereocopolymers as Determined by $^{13}C(^{1}H)$ N.M.R.", 1983, *Polymer*, v. 24, pp. 53–59).

F. Kohn, J. Van Don Berg, G. Van De Ridder and J. Feijen ("The Ring–Opening Polymerization of D,L–Lactide in the Melt Initiated with Tetraphenyltin". 1984, *Journal of Applied Polymer Science*, v. 29, pp. 4265–4277).

H. Kricheldorf and A. Serra ("Polylactones 6. Influence of Various Metal Salts on the Optical Purity of Poly(L–lactide)", 1985, *Polymer Bulletin*, v. 14, pp. 497–502).

A. Chawla and T. Chang ("In–Vivo Degradation of Poly(lactic acid) of Different Molecular Weights", 1985, *Biomat., Med. Dev., Art. Org.*, v. 13, pp. 153–162).

I. McNeill and H. Leiper ("Degradation Studies of Some Polyesters and Polycarbonated—1. Polylactide: General Features of the Degradation Under Programmed Heating Conditions", 1985, *Polymer Degradation and Stability*, v. 11, pp. 267–285).

I. McNeill and H. Leiper ("Degradation Studes of Some Polyesters and Polycarbonates—2. Polylactide: Degradation Under Isothermal Conditions, Thermal Degradation Mechanism and Photolysis of the Polymer", 1985, Polymer Degradation and Stability, v. 11, pp. 309–326).

Makino et al. ("Preparation and in Vitro Degradation Properties of Polylactide Microcapsules", 1985, *Chem. Pharm. Bull.*, v. 33, pp. 1195–1201.

Dr. Garozzo, M. Giuffrida and G. Montaudo ("Primary Thermal Decomposition Processes in Aliphatic Polyesters Investigated by Chemical Ionization Mass Spectrometry", 1986, *Macromolecules*, v. 19, pp. 1643–1649).

"Irganox®", 1078 Antioxidant and Thermal Stabilizer, (published on an unknown date in 1986 by Ciba–Geigy Corporation, Three Skyline Drive, Hawthorne, NY 10532).

J. Leenslag and A. Pennings ("Synthesis of high–molecular–welght poly(L–lactide) initiated with tin 2–ethylhexanoate", 1987, *Makromol. Chem.*, v. 188, pp. 1809–1814).

Nakamura et al. "Surgical Application of Biodegradable Films Prepared from Lactide–ϵ–Caprolacatone Copolymers", 1987, *Bio. Materials and Clinical Applications*, v. 7, pp. 759–765.

H. Kricheldorf, M. Berl and N. Schamagl ("Polymerization Mechanism of Metal Alkoxide Initiated olymerizations of Lactide nad Various Lactones", 1988, *Makromol.*, v. 21, pp. 286–293).

K. Jamshidi et al., *Thermal Characterization of Polylactides*, 1988, Polymer, v. 29, pp. 2229–2234.

M. Vert, *Bioresorbable Polymers for Temporary Therapeutic Applications*, 1989, Die Angwandte Makromolekulare Chemie, v. 166–167, pp. 155–168.

*Hydrolytic Stability/Corrosivity of Phosphate Costabilizers*, Technical Bulletin 89–04, published on an unknown date in 1989, by Star Laboratory, Additives Division, Ciba–Geigy Corporation, Ardsley, NY 10502.

*GE Specialty Chemicals Product Guide CA–4001E*, published on an unknown date in 1989, by General Electric Company, 5th and Avery Street, Parkersburg, WV 26102.

*Tinuvin® 123 Hindered Aminoether Light Stabilizer for Coatings*, published on an unknown date in 1989, by Ciba–Geigy Corporation, Three Skyline Drive, Hawthorne, NY 10532.

*Irganox® B–Blends Antioxidants and Process Stabilizers for Polymers*, published on an unknown date in Mar., 1990, by Ciba–Geigy Corporation, Three Skyline Drive, Hawthorne, NY 10532.

*Naugard® 445, Specialty Chemicals*, a product brochure published on or before May 1, 1990, by Uniroyal Chemical Company, Inc., Middlebury, CT 06749.

*Ethanox® 398 Antioxidant, the First Fluorophosphonite Antioxidant*. published on or before an unknown date in Oct., 1990, by Ethyl Corporation, 451 Florida Blvd., Baton Rouge, LA 70801.

*The Resomer® Resorbable Polyesters*, published on or before an unknown date in Feb., 1991 by Boehringer Ingelheim KG, D–6507 Ingelheim, W. Germany.

P. Klemchuk, *Introduction to Polymer Degradation*, lecture notes distributed at a seminar entitled: Principles of Polymer Degradation and Stabilization in Orlando, Florida, Oct. 28–30, 1991, sponsored by The Institute of Materials Science, State University of New York at New Paltz.

R. Thomas, *"Degradation and Stabilization of Engineering Polymers*, lecture notes distribued at a seminar entitled" Principles of Polymer Degradation and Stabilization in Orlando, Florida, Oct. 28–30, 1991, sponsored by The Institute of Materials Science, State University of New York at New Paltz.

W. Enlow, *"Process Stabilization with Phosphite Antioxidants*, lecture notes distributed at a seminar entitled" Principles of Polymer Degradation and Stabilization in Orlando, Florida, Oct. 28–30, 1991, sponsored by The Institute of Materials Science, State University of New York at New Paltz.

*Naugard® XL–1 Specialty Chemicals*, product brochure published on an unknown date in Feb., 1992, by Uniroyal Chemical Co., Inc., Middlebury, CT 06749.

Sir John Meurig Thomas, *Solid Acid Catalysts*, Apr. 1992, Scientific American, pp. 112–118.

*Argus Product Data, Argus® Dimyristyl Thiodipropionate*, published on or before an unknown date in Aug., 1992 by Argus Division, Witco Corporation, 633 Court Street, Brooklyn, NY 11231–2193.

*Argus Product Data, Argus® Distearyl Thiodipropionate*, published on or before an unknown date in Aug., 1992 by Argus Division, Witco Corporation, 633 Court Street, Brooklyn, NY 11231–2193.

*Argus Product Data, Mark® 2140 Pentaerythrityl Octylthiopropionate*, published on or before an unknown date in Aug., 1992, by Argus Division, Witco Corporation, 633 Court Street, Brooklyn, NY 11231–2193.

*Arugs Thiochemical Product Data, Argus® Dileuryl Thiodipropionate*, published on or before an unknown date in Aug., 1992, by Argus Division, Witco Corporation, 633 Court Street, Brooklyn, NY 11231–2193.

*Argus Product Data, Seenox® 412S Pentaerythritol Tetrakas (B–Laurylthiopropionate,* published on or before an unknown date in Aug., 1992, by Argus Division, Witco Corporation, 633 Court Street, Brooklyn, NY 11231–2193.

*Irganox® 1010,* a product brochure published on or before an unknown date in Aug., 1992, by Ciba–Geigy Corporation, Three Skyline Drive, Hawthorne, NY 10532.

*Irganox® MD 1024, Metal Deactivator/Antioxidant,* published on an unknown date prior to Aug., 1992 by Ciba–Geigy Corporation, Three Skyline Drive, Hawthorne, NY 10532.

*Tinuvin® 622LD Low Dust, Hindered Amine Light Stabilizer for Polymers FDA–Cleared for Polyolefins,* published on an unknown date before Aug., 1992 by Ciba–Geigy Corporation, Three Skyline Drive, Hawthorne, NY 10532.

P.V. Bonsignore et al., *Poly(lactic acid) Degradable Plastics, Coatings, and Biners,* TAPPI Proceedings (Nonwovens Conference), 1992, pp. 129–140.

PAPER HAVING A MELT-STABLE LACTIDE POLYMER COATING AND PROCESS FOR MANUFACTURE THEREOF

CROSS-REFERENCE TO RELATED APPLICATIONS

The present application is a continuation application of U.S. application Ser. No. 08/034,099, filed Mar. 22, 1993, and which issued as U.S. Pat. No. 5,475,080 on Dec. 12, 1995. U.S. application Ser. No. 08/034,099 is a continuation-in-part application of U.S. application Ser. No. 07/955,690, which was filed on Oct. 2, 1992, and which issued as U.S. Pat. No. 5,338,822 on Aug. 16, 1994. U.S. Pat. Nos. 5,475,080 and 5,338,822 are incorporated herein by reference.

BACKGROUND OF THE INVENTION

1. Field of the Invention

The present invention relates to a paper product having a melt-stable, biodegradable lactide polymer composition coated thereon and a process for manufacturing paper products coated with such melt-stable, biodegradable lactide polymers.

2. Description of the Prior Art

The need for coated paper is well established. Paper is coated with either polymeric or wax coatings for various reasons. These reasons include increasing the strength of the paper stock, imparting water resistance, enhancing gloss, improving barrier properties and the like.

In light of depleting sources of cellulosic fiber over the last decade, repulping of paper and the reuse of the cellulosic fiber recovered in the repulping process has accelerated. A typical repulping process involves mechanical agitation of the paper. Often the repulping environment involves water, heat or other harsh conditions such as an acidic or alkaline solution.

A problem that occurs with repulping coated paper is the disposal or recycling of the coating which is liberated during the repulp process. Currently, coatings such as polyethylene are popular for their superior coating properties. However, in repulping processes, papers coated with polyethylene are not easily repulped since polyethylene is typically not broken down by the conditions of the repulping process.

Coatings have been developed which are represented to be "repulpable." These are materials which purportedly have adequate properties as paper coatings, and when exposed to conditions of repulping, either dissolve or disperse. In a solution or dispersion, it is claimed that these materials will pass through screens and other filtering steps and pass out with the waste water before the repulping step.

Although these coatings have been extensively used, many problems have been encountered with their use. Often the coatings are not clear or glossy. Some coatings may also be unduly sensitive to water.

Disposal is a major problem associated with both repulpable and non-repulpable coating. For coatings which are recovered during the repulp process, there is no value in the recovered material and therefore these coatings represent waste generally disposed of in a landfill. For the coatings which pass through the filters and screens of the process, these materials end up in the waste water and may pose a problem for the waste water treatment plants.

Although not believed to be known as a paper coating material, the use of lactic acid and lactide to manufacture a biodegradable polymer is well-known in the medical industry. As disclosed by Nieuwenhuis et al. (U.S. Pat. No. 5,053,485), such polymers have been used for making biodegradable sutures, clamps, bone plates and biologically active controlled release devices. Processes developed for the manufacture of polymers to be utilized in the medical industry have incorporated techniques which respond to the need for high purity and biocompatability in the final product. These processes were designed to produce small volumes of high dollar-value products, with less emphasis on manufacturing cost and yield.

In order to meet projected needs for biodegradable packaging materials, others have endeavored to optimize lactide polymer processing systems. Gruber et al. (U.S. Pat. No. 5,142,023) disclose a continuous process for the manufacture of lactide polymers with controlled optical purity from lactic acid having physical properties suitable for replacing present petrochemical-based polymers.

Generally, manufacturers of polymers utilizing processes such as those disclosed by Gruber et al. will convert raw material monomers into polymer beads, resins or other pelletized or powdered products. The polymer in this form is then sold to end users who convert, i.e., extrude, blow-mold, cast films, blow films, thermoform, injection-mold or fiber-spin the polymer at elevated temperatures to form useful articles. The above processes are collectively referred to as melt-processing. Polymers produced by processes such as those disclosed by Gruber et al., which are to be sold commercially as beads, resins, powders or other non-finished solid forms are generally referred to collectively as polymer resins.

Prior to the present invention, it is believed that there has been no disclosure of a combination of composition control and melt stability requirements which will lead to the production of commercially viable lactide polymer coatings for cellulosic paper.

It is generally known that lactide polymers or poly (lactide) are unstable. The concept of instability has both negative and positive aspects. A positive aspect is the biodegradation or other forms of degradation which occur when lactide polymers or articles manufactured from lactide polymers are discarded or composted after completing their useful life. A negative aspect of such instability is the degradation of lactide polymers during processing at elevated temperatures as, for example, during melt-processing by end-user purchasers of polymer resins. Thus, the same properties that make lactide polymers desirable as replacements for non-degradable petrochemical polymers also creates undesirable effects during processing which must be overcome.

Lactide polymer degradation at elevated temperature has been the subject of several studies, including: I. C. McNeill and H. A. Leiper, *Polymer Degradation and Stability*, vol. 11, pp. 267–285 (1985); I. C. McNeill and H. A. Leiper, *Polymer Degradation and Stability*, vol. 11, pp. 309–326 (1985); M. C. Gupta and V. G. Deshmukh, *Colloid & Polymer Science*, vol. 260, pp. 308–311 (1982); M. C. Gupta and V. G. Deshmukh, *Colloid & Polymer Science*, vol. 260, pp. 514–517 (1982); Ingo Luderwald, *Dev. Polymer Degradation*, vol. 2, pp. 77–98 (1979); Domenico Garozzo, Mario Giuffrida, and Giorgio Montaudo, *Macromolecules*, vol. 19, pp. 1643–1649 (1986); and, K. Jamshidi, S. H. Hyon and Y. Ikada, *Polymer*, vol. 29, pp. 2229–2234 (1988).

It is known that lactide polymers exhibit an equilibrium relationship with lactide as represented by the reaction below:

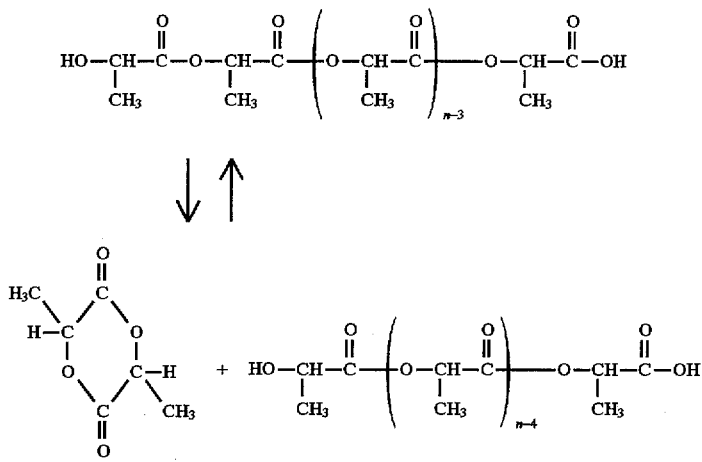

No consensus has been reached as to what the primary degradation pathways are at elevated processing temperatures. One of the proposed reaction pathways includes the reaction of a hydroxyl end group in a "back-biting" reaction to form lactide. This equilibrium reaction is illustrated above. Other proposed reaction pathways include: reaction of the hydroxyl end group in a "back-biting" reaction to form cyclic oligomers, chain scission through hydrolysis of the ester bonds, an intramolecular beta-elimination reaction producing a new acid end group and an unsaturated carbon-carbon bond, and radical chain decomposition reactions. Regardless of the mechanism or mechanisms involved, the fact that substantial degradation occurs at elevated temperatures, such as those used by melt-processors, creates an obstacle to use of lactide polymers as a replacement for petrochemical-based polymers. It is apparent that degradation of the polymer during melt-processing must be reduced to a commercially acceptable rate while the polymer maintains the qualities of biodegradation or compostability which make it so desirable. It is believed this problem has not been addressed prior to the developments disclosed herein.

As indicated above, poly(lactide)s have been produced in the past, but primarily for use in medical devices. These polymers exhibit biodegradability, but also a more stringent requirement of being bioresorbable or biocompatible. As disclosed by M. Vert, Die Ingwandte Makromolekulare Chemie, vol. 166–167, pp. 155–168 (1989), "The use of additives is precluded because they can leach out easily in body fluids and then be recognized as toxic, or, at least, they can be the source of fast aging with loss of the properties which motivated their use. Therefore, it is much more suitable to achieve property adjustment through chemical or physical structure factors, even if aging is still a problem." Thus, work aimed at the bioresorbable or biocompatible market focused on poly(lactide) and blends which did not include any additives.

Other disclosures in the medical area include Nieuwenhuis (European Patent No. 0 314 245), Nieuwenhuis (U.S. Pat. No. 5,053,485), Eitenmuller (U.S. Pat. No. 5,108,399), Shinoda (U.S. Pat. No. 5,041,529), Fouty (Canadian Patent No. 808,731), Fouty (Canadian Patent No. 923,245), Schneider (Canadian Patent No. 863,673), and Nakamura et al., Bio. Materials and Clinical Applications, Vol. 7, p. 759 (1987). As disclosed in these references, in the high value, low volume medical specialty market, poly(lactide) or lactide polymers and copolymers can be given the required physical properties by generating lactide of very high purity by means of such methods as solvent extraction or recrystallization followed by polymerization. The polymer generated from this high purity lactide is a very high molecular weight product which will retain its physical properties even if substantial degradation occurs and the molecular weight drops significantly during processing. Also, the polymer may be precipitated from a solvent in order to remove residual monomer and catalysts. Each of these treatments add stability to the polymer, but clearly at a high cost which would not be feasible for lactide polymer compositions which are to be used to replace inexpensive petrochemical-based polymers in packaging, paper-coating and other non-medical applications.

Furthermore, it is well-known that an increase in molecular weight generally results in an increase in a polymer's viscosity. A viscosity which is too high can prevent melt-processing of the polymer due to physical/mechanical limitations of the melt-processing equipment. Melt-processing of higher molecular weight polymers generally requires the use of increased temperatures to sufficiently reduce viscosity so that processing can proceed. However, there is an upper limit to temperatures used during processing. Increased temperatures increase degradation of the lactide polymer, as the previously-cited studies disclose.

Jamshidi et al., Polymer, Vol. 29, pp. 2229–2234 (1988) disclose that the glass transition temperature of a lactide polymer, $T_g$, plateaus at about 57° C. for poly(lactide) having a number average molecular weight of greater than 10,000. It is also disclosed that the melting point, $T_m$, of poly (L-lactide) levels off at about 184° C. for semi-crystalline lactide polymers having a number average molecular weight of about 70,000 or higher. This indicates that at a relatively low molecular weight, at least some physical properties of lactide polymers plateau and remain constant.

Sinclair et al. (U.S. Pat. No. 5,180,765) disclose the use of residual monomer, lactic acid or lactic acid oligomers to plasticize poly(lactide) polymers, with plasticizer levels of 2–60 percent. Loomis (U.S. Pat. No. 5,076,983) discloses a process for manufacturing a self-supporting film in which the oligomers of hydroxy acids are used as plasticizing agents. Loomis and Sinclair et al. disclose that the use of a plasticizer such as lactide or lactic acid is beneficial to produce more flexible materials which are considered to be preferable. Sinclair et al., however, disclose that residual monomer can deposit out on rollers during processing.

Loomis also recognizes that excessive levels of plasticizer can cause unevenness in films and may separate and stick to and foul drums used for casting such films. Furthermore, it has been recognized these problems may also lead to defects in the paper coating or other films. Thus, plasticizing as recommended, negatively impacts melt-processability.

Accordingly, a need exists for a lactide polymer coating which is melt-stable under the elevated temperatures common to melt-processing. The needed melt-stable polymer composition must also exhibit sufficient compostability or degradability after its useful life as a coating. Further, the melt-stable polymer must be processable in existing melt-processing equipment, by exhibiting sufficiently low viscosities at melt-processing temperatures while polymer degradation and lactide formation remains below a point of substantial degradation and does not cause excessive fouling of processing equipment. Furthermore, the polymer lactide must retain its molecular weight, viscosity and other physical properties within commercially-acceptable levels through the coating process. It will be further appreciated that a need also exists for a process for coating such polymer compositions. The present invention addresses these needs as well as other problems associated with existing lactide polymer compositions and manufacturing processes. The present invention also offers further advantages over the prior art, and solves other problems associated therewith.

SUMMARY OF THE INVENTION

According to the present invention, a paper product is provided having a lactide polymer coating thereon. The polymeric coating is made from a melt-stable lactide polymer composition comprising: a plurality of poly(lactide) polymer chains having a number average molecular weight of from about 10,000 to about 200,000; lactide in a concentration of less than about 5 percent by weight; and water in a concentration of less than about 2,000 parts per million. A process for the manufacture of the coated paper is also provided. For the purposes of the present invention, paper may comprise cellulose, lignin, hemicellulose, synthetic fibers or mixtures thereof.

Optionally, stabilizing agents in the form of anti-oxidants and water scavengers may be added. Further, plasticizers and/or anti-blocking agents may be added. The resultant coating has a high gloss, excellent adhesion, heat sealability, is biodegradable and may be repulped in an economically efficient manner.

Poly(lactide) is a polymeric material which offers unique advantages as a paper coating not only in the repulping process, but in the application process and the coated paper's performance.

Poly(lactide) offers numerous advantages in the repulping process. Under conditions of neutral pH and moderate temperatures (120° F.), poly(lactide) will break up more easily than polyethylene coatings due both to the greater water susceptibility and the lower impact strength. The fragments of poly(lactide) may be recovered in the screens and either recycled for their lactic acid value or composted.

Under the more severe repulping conditions which includes pH of 10 or greater, high temperature, and optional surfactants, poly(lactide) will degrade to the extent that it disperses in water and passes through the screens. Again, the fragments of poly(lactide) may be recovered and recycled or composted. Because of poly(lactide)'s ability to biodegrade, the polymer should pose no problems in the waste water treatment stage.

Poly(lactide) offers advantages in the application of the polymer to the paper in a melt extrusion process. One problem that is sometimes encountered in the paper coating process is poor adhesion of the polymer to the surface of the paper. Two characteristics of poly(lactides) lend themselves to enhanced adhesion: low viscosity and high polarity. Mechanical adhesion, the interlocking of surfaces, increases as the polymer coating penetrates the porous surface of the paper. The rate of penetration of the coating increases as the viscosity decreases. An advantage of poly(lactide) is that the viscosity is quite low at typical melt extrusion temperatures. Thus, poly(lactide) penetrates the paper well resulting in enhanced adhesion. Also, because the paper surface is typically polar for most fibers, the high polarity of the poly(lactide) offers many dipole-dipole interactions, further resulting in enhanced adhesion.

One of the problems encountered in coating paper from a melt is due to the surface roughness of the paper. On a microscopic scale the surface of the paper resembles a series of peaks and valleys. For a coating to be pinhole-free and have high gloss, it must bridge the gap across the valleys. Gloss will diminish as the roughness of the surface of the coating increases. Applicants believe that the ability of the coating to maintain a smooth, coherent film despite the roughness of the paper is related to the surface energy of the coating. As the surface energy of a coating increases, the driving force to remain intact and to minimize surface area increases, therefore the tendency to form a smooth, coherent, high gloss coating increases. Poly(lactide) is a material with a relatively high surface energy, when compared to other common coating materials.

The coating of the present invention exhibits a higher surface energy then typical polyethylene or polypropylene films. These hydrocarbon films have a surface energy in the range of 30–33 dynes/cm. In order to produce a satisfactory printing surface, these films must first be modified to raise their surface energy to 35–38 dynes/cm. This not only increases the costs associated with production of the films, but the modification treatment will diffuse into the film and will produce an unsatisfactory printing surface.

The surface energy of substantially pure poly(lactide) films of the present invention is about 44 dynes/cm. This leads to a surface with satisfactory printing characteristics without surface modification. Fillers may reduce the surface energy down to about 35 dynes/cm. Additionally, inks which are typically more difficult to apply onto paper coatings, like water based inks, may be applied directly to poly(lactide).

Poly(lactide) is a relatively low viscosity polymer which allows the extrusion coating to be done at lower temperatures than traditional coatings. This results in a cost savings to the converter because the extrusion equipment will not require as much power when run at lower temperatures.

Heat sealability is also a property of coatings which is desirable. Poly(lactide) can be heat sealed at temperatures lower than 300° F., at pressures lower than 60 psi, and at times less than 0.5 sec.

A significant advantage of poly(lactide) over many coatings used today such as polyethylene is its biodegradability. As outlined above, in the prior art repulping processes, the coating generally is filtered out. This filtrate must then be disposed of. The continued depletion of landfill space and the problems associated with incineration of waste have led to the need for development of a truly biodegradable polymer coating to be utilized as substitutes for non-biodegradable or partially biodegradable petrochemical-based polymer coatings.

The above described features and advantages along with various other advantages and features of novelty are pointed out with particularity in the claims of the present application. However, for a better understanding of the invention, its advantages, and objects attained by its use, reference should be made to the drawings which form a further part of the present application and to the accompanying descriptive matter in which there is illustrated and described preferred embodiments of the present invention.

BRIEF DESCRIPTION OF THE DRAWINGS

In the drawings, in which like reference numerals indicate corresponding parts or elements of preferred embodiments of the present invention throughout the several views.

DETAILED DESCRIPTION OF THE PREFERRED EMBODIMENT(S)

Figure 1:
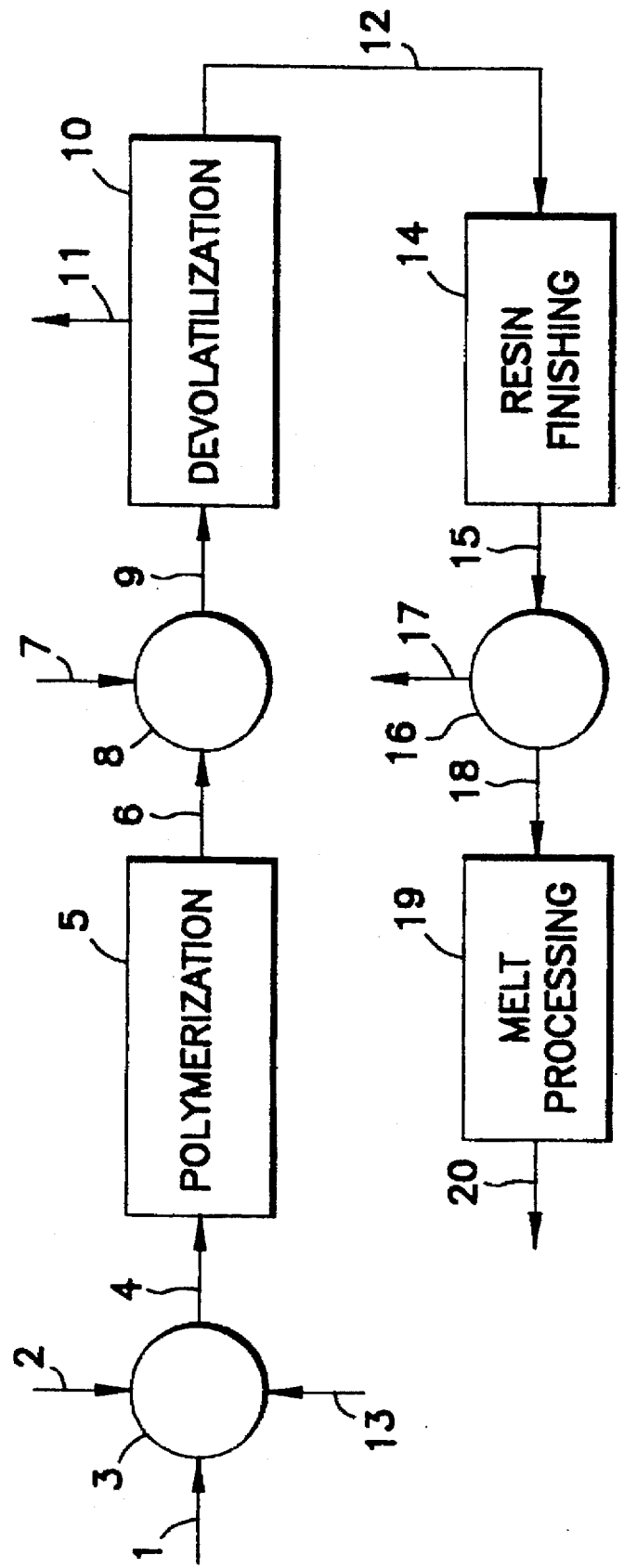
FIG. 1 is a schematic representation of a preferred process for the manufacture of a melt-stable lactide polymer composition.

The lactide polymer compositions used in paper coating disclosed herein focus on meeting the requirements of the end user melt-processor of a lactide polymer resin such as that produced from a process disclosed by Gruber et al. However, the present invention is directed to a poly(lactide) coating and is not limited to the lactide polymer composition or process of Gruber et al. Any lactide polymer composition, which comes within the scope of this invention, may be used as a coating. As disclosed herein, the problems with degradation, fouling, and lactide formation during melt-processing of lactide polymers are addressed through suggested ranges of molecular weights and compositional limits on impurities such as residual monomer, water and catalyst along with the use of stabilizing agents and catalyst-deactivating agents.

In general, according to the present invention, a melt-stable lactide polymer coating for paper and a process for manufacturing a melt-stable lactide polymer coating are disclosed. Lactide polymers are useful due to their biodegradable nature. Furthermore, lactide polymers are compostable as illustrated in Example 15 below. Applicants believe the hydrolysis of the ester may be the key to or the first step in degradation of a lactide polymer composition. The mechanism of degradation is not key to the coating of the present invention, however it must be recognized that such degradation makes lactide polymers desirable as replacements for presently-utilized non-degradable petrochemical-based polymers used for coatings.

Applicants have found that the instability of lactide polymers which leads to the beneficial degradation discussed above also creates processing problems. These processing problems include generation of lactide monomer at elevated temperatures and loss in molecular weight believed due to chain scission degradation of the ester bonds and other depolymerization reactions which are not completely understood. No consensus has been reached as to what are the primary degradation pathways at elevated processing temperatures. As previously disclosed, these may include such pathways as equilibrium-driven depolymerization of lactide polymers to form lactide and chain scission through hydrolysis of the ester bonds along with other pathways. For purposes of the present invention, the exact mechanism of degradation at elevated temperatures is not critical.

It is to be understood, however, that degradation of lactide polymers is both beneficial and detrimental. Benefits derive from degradability when articles manufactured from such polymers are discarded. The same or similar types of degradation are detrimental if they occur during processing or prior to the end of the article's useful life.

Melt-Processing

It is believed that a manufacturer of lactide polymers from a lactide monomer will produce a lactide polymer resin which is in the form of beads or pellets. The melt-processor will convert the resin to a useful article by elevating the temperature of the resin above at least its glass transition temperature but normally higher. Common melt-processing techniques include extrusion, blow-molding, injection-molding, fiber-spinning, film-blowing, film-casting and the like. It is to be understood that the conditions of elevated temperature used in melt-processing cause degradation of lactide polymers during processing. Degradation under melt-processing conditions is shown experimentally in Example 7 based on equilibrium, Example 10 based on catalyst concentration, Example 11 based on catalyst activity, Example 13 based on use of stabilizers and Example 14 based on moisture content. As can be seen in these examples, it is understood that several factors appear to affect the rate of degradation during melt-processing. Applicants have addressed these factors in a combination of compositional requirements and the addition of stabilizing or catalyst-deactivating agents to result in a polymer of lactide which is melt-stable.

In addition, melt-processing frequently produces some proportion of trimmed or rejected material. Environmental concerns and economical efficiencies dictate that this material be reused, typically by regrinding and adding back the material into the polymer feed. This introduces additional thermal stress on the polymer and increases the need for a melt-stable polymer composition.

Melt Stability

The lactide polymers of the present invention are melt-stable. By "melt-stable" it is meant generally that the lactide polymer, when subjected to melt-processing techniques, adequately maintains its physical properties and does not generate by-products in sufficient quantity to foul or coat processing equipment. The melt-stable lactide polymer exhibits reduced degradation and/or reduced lactide formation relative to known lactide polymers. It is to be understood that degradation will occur during melt-processing. The compositional requirements and use of stabilizing agents as disclosed herein reduces the degree of such degradation to a point where physical properties are not significantly affected by melt-processing and fouling by impurities or degradation by-products such as lactide does not occur. Furthermore, the melt-stable polymer should be melt-processable in melt-processing equipment such as that available commercially. Further, the polymer will preferably retain adequate molecular weight and viscosity. The polymer should preferably have sufficiently low viscosity at the temperature of melt-processing so that the coating equipment may create an acceptable coating. The temperature at which this viscosity is sufficiently low will preferably also be below a temperature at which substantial degradation occurs.

Polymer Composition

The melt-stable lactide polymer coating of the present invention comprises a plurality of poly(lactide) polymer chains having a number average molecular weight from about 10,000 to about 200,000. In a preferred composition, the number average molecular weight ranges from about 20,000 to about 175,000. In the most preferred composition, the number average molecular weight ranges from about 40,000 to about 150,000. As detailed in Example 9, it appears that the physical properties such as modulus, tensile strength, percentage elongation at break, impact strength, flexural modulus, and flexural strength remain statistically constant when the lactide polymer samples are above a threshold molecular weight. The lower limit of molecular weight of the polymer compositions of the present invention is set at a point above the threshold in order to result in a lactide polymer with predictable physical properties upon melt-processing. As detailed in Example 22, there is a practical upper limit on molecular weight based on increased viscosity with increased molecular weight. In order to melt-process a high molecular weight lactide polymer, the melt-processing temperature must be increased to reduce the viscosity of the polymer. As pointed out in the Examples, the exact upper limit on molecular weight must be determined for each melt-processing application in that required viscosities vary and residence time within the melt-processing equipment will also vary. Thus, the degree of degradation in each type of processing system will also vary. Based on the disclosure of Example 22, it is believed that one could determine the suitable molecular weight upper limit for meeting the viscosity and degradation requirements in any application.

The melt-stable lactide polymer compositions in the preferred embodiment are the reaction product of polymerizing a lactide mixture comprising about 3 percent by weight to about 50 percent by weight meso-lactide with the remaining percent by weight L-lactide and/or D-lactide. The more preferred embodiment has a mixture having a meso-lactide concentration of about 7 percent by weight to about 50 percent by weight and the remaining percent by weight L-lactide and/or D-lactide. In the most preferred embodiment, the mixture has a concentration of meso-lactide of about 10 percent by weight to about 50 percent by weight with the remaining percent by weight being L-lactide and/or D-lactide. The optical composition disclosed includes the benefit of utilizing meso-lactide as disclosed by Gruber et al. In preferred compositions of the present invention, the melt-stable lactide polymer is essentially amorphous. As detailed in Example 15, amorphous lactide polymers exhibit superior degradability when subjected to a compost test.

Applicants recognize that an essentially amorphous lactide polymer may have some crystallinity. Crystalline poly L-lactide exhibits an endotherm of roughly 92 Joules per gram at its melting temperature of 170°–190° C. The melting point changes with composition. The degree of crystallinity is roughly proportional to the endotherm on melting. For purposes of the present invention, in preferred embodiments, it is meant by an amorphous or non-crystalline poly(lactide) to be a poly(lactide) or lactide polymer which exhibits a melting endotherm of less than about 10 Joules per gram in the temperature range of 130°–200° C.

The residual monomer concentration in the melt-stable lactide polymer composition is less than about 5 percent by weight. In a preferred composition the concentration of lactide in the polymer is less than about 2 percent by weight, a more preferred composition is less than about 1 percent by weight, and a most preferred composition is less than about 0.5 percent by weight. Contrary to disclosures in the art, Applicants have found that the monomer cannot be used as a plasticizing agent in the resin of the present invention due to significant fouling or plating out problems in coating equipment. As detailed in Example 16, it is believed the low levels of monomer concentration do not plasticize the final polymer.

The water concentration within the melt-stable lactide polymer composition is less than about 2,000 parts-per-million. Preferably this concentration is less than 1,000 parts-per-million and more preferably less than about 300 parts-per-million. As detailed in Example 14, the polymer melt-stability is significantly affected by moisture content. Thus, the melt-stable polymer of the present invention must have the water removed prior to melt-processing. Applicants recognize that water concentration may be reduced prior to processing the polymerized lactide to a resin. Thus, moisture control could be accomplished by packaging such resins in a manner which prevents moisture from contacting the already-dry resin. Alternatively, the moisture content may be reduced at the melt-processor's facility just prior to the melt-processing step in a dryer. Example 14 details the benefit of drying just prior to melt-processing and also details the problems encountered due to water uptake in a polymer resin if not stored in a manner in which moisture exposure is prevented or if not dried prior to melt-processing. As detailed in these examples, Applicants have found that the presence of water causes excessive loss of molecular weight which may affect the physical properties of the melt-processed polymer.

In a preferred composition of the present invention, a stabilizing agent is included in the polymer formulation to reduce degradation of the polymer during production, devolatilization, drying and melt processing by the end user. The stabilizing agents recognized as useful in the present polymer coating compositions may include antioxidants and/or water scavengers. Preferred antioxidants are phosphite-containing compounds, hindered phenolic compounds or other phenolic compounds. The antioxidants include such compounds as trialkyl phosphites, mixed alkyl/aryl phosphites, alkylated aryl phosphites, sterically hindered aryl phosphites, aliphatic spirocyclic phosphites, sterically hindered phenyl spirocyclics, sterically hindered bisphosphonites, hydroxyphenyl propionates, hydroxy benzyls, alkylidene bisphenols, alkyl phenols, aromatic amines, thioethers, hindered amines, hydroquinones and mixtures thereof. As detailed in Example 13, many commercially-available stabilizing agents have been tested and fall within the scope of the present melt-stable lactide polymer coating composition. Biodegradable antioxidants are particularly preferred.

The water scavengers which may be utilized in preferred embodiments of the melt-stable lactide polymer coating composition include: carbodiimides, anhydrides, acyl chlorides, isocyanates, alkoxy silanes, and desiccant materials such as clay, alumina, silica gel, zeolites, calcium chloride, calcium carbonate, sodium sulfate, bicarbonates or any other compound which ties up water. Preferably the water scavenger is degradable or compostable. Example 19 details the benefits of utilizing a water scavenger.

In a preferred composition of the present invention, a plasticizer is included in the polymer formulation to improve the coating quality of the lactide polymer. More particularly, plasticizers reduce the glass transition temperature of poly (lactide), which aides in processing and coating the polymer at lower temperatures and may improve flexibility and reduce cracking tendencies of the coated product.

Selection of a plasticizing agent requires screening of many potential compounds and consideration of several criteria. For use in a biodegradable coating the preferred plasticizer is to be biodegradable, non-toxic, compatible with the resin and relatively nonvolatile.

Plasticizers in the general classes of alkyl or aliphatic esters, ether, and multi-functional esters and/or ethers are preferred. These include alkyl phosphate esters, dialkylether diesters, tricarboxylic esters, epoxidized oils and esters, polyesters, polyglycol diesters, alkyl alkylether diesters, aliphatic diesters, alkylether monoesters, citrate esters, dicarboxylic esters, vegetable oils and their derivatives, and esters of glycerine. Most preferred plasticizers are tricarboxylic esters, citrate esters, esters of glycerine and dicarboxylic esters. These esters are anticipated to be biodegradable. Plasticizers containing aromatic functionality or halogens are not preferred because of their possible negative impact on the environment.

For example, appropriate non-toxic character is exhibited by triethyl citrate, acetyltriethyl citrate, tri-n-butyl citrate, acetyltri-n-butyl citrate, acetyltri-n-hexyl citrate, n-butyryltri-n-hexyl citrate and dioctyl adipate.

Appropriate compatibility is exhibited by acetyltri-n-butyl citrate and dioctyl adipate. Other compatible plasticizers include any plasticizers or combination of plasticizers which can be blended with poly(lactide) and are either miscible with poly(lactide) or which form a mechanically stable blend. Corn oil and mineral oil were found to be incompatible when used alone with poly(lactide) because of phase separation (not mechanically stable) and migration of the plasticizer.

Volatility is determined by the vapor pressure of the plasticizer. An appropriate plasticizer must be sufficiently non-volatile such that the plasticizer stays substantially in the resin formulation throughout the process needed to produce the coating. Excessive volatility can lead to fouling of process equipment, which is observed when producing films by melt processing poly(lactide) with a high lactide content. This is demonstrated in Example 6. Preferred plasticizers should have a vapor pressure of less than about 10 mm Hg at 170° C., more preferred plasticizers should have a vapor pressure of less than 10 mm Hg at 200° C. Lactide, which is not a preferred plasticizer, has a vapor pressure of about 40 mm Hg at 170° C. Example 25 highlights useful plasticizers for the present invention.

In a preferred composition, fillers may be useful to prevent blocking or sticking of the coated product during storage and transport. Inorganic fillers include clays and minerals, either surface modified or not. Examples include talc, silica, mica, kaolin, titanium dioxide, and wollastonite. Preferred inorganic fillers are environmentally stable and non-toxic.

Organic fillers include a variety of forest and agricultural products, either with or without modification. Examples include cellulose, wheat, starch, modified starch, chitin, chitosan, keratin, cellulosic materials derived from agricultural products, gluten, nut shell flour, wood flour, corn cob flour, and guar gum. Preferred organic fillers are derived from renewable sources and are biodegradable. Fillers may be used either alone or as mixtures of two or more fillers. Example 23 highlights useful anti-blocking agents for the present invention.

Surface treatments may also be used to reduce blocking. Such treatments include dusting the surface with materials which reduce the surface contact between the poly(lactide) based coating and the adjacent surface. Examples of materials which may be used in surface treatments include talc, silica, corn starch, corn meal, latex spheres or other particulates.

For certain applications, it is desirable for the coating to have good slip properties. Lubricating solids such as fluoropolymer powders or graphite are sometimes incorporated into materials to increase slip properties. The fatty acid esters or hydrocarbon waxes commonly used as lubricants for the melt state, are gradually exuded, if used in very high concentrations, thus yielding to permanent lubricating effects. Certain additives migrate so strongly to the surface, even during cooling, that a uniform invisibly thin coating is formed. Thus, these slip agents may be important in the production of coatings which are used in automatic packaging machines.

Antistatic agents may be employed in the present invention. Antistatic agents are surfactants which can be subdivided into cationic, anionic, and nonionic agents.

With regard to cationic compounds, the active molecule part generally consists of a voluminous cation which often contains a long alkyl residue (e.g. a quaternary ammonium, phosphonium or sulfonium salt) where by the quaternary group can also occur in a ring system (e.g. imidazoline). In most cases, the anion is the chloride, methosulfate or nitrate originating from the quaternization process.

In the anionic compounds, the active molecule part in this class of compounds is the anion, mostly an alkyl sulfonate, sulfate or phosphate, a dithiocarbamate or carboxylate. Alkali metals often serve as cations.

Nonionic antistatic agents are uncharged surface-active molecules of a significantly lower polarity than the above mentioned ionic, compounds and include polyethylene glycol esters or ethers, fatty acid esters or ethanolamides, mono- or diglycerides or ethyoxylated fatty amines.

Pigments or color agents may also be added as necessary. Examples include titanium dioxide, clays, calcium carbonacalcium carbonate, talc, mica, silica, silicates, iron oxides and hydroxides, carbon black and magnesium oxide.

In the manufacture of the melt-stable lactide polymer compositions of the present invention, the reaction to polymerize lactide is catalyzed. Many catalysts have been cited in literature for use in the ring-opening polymerization of lactones. These include but are not limited to: $SnCl_2$, $SnBr_2$, $SnCl_4$, $SnBr_4$, aluminum alkoxides, tin alkoxides, zinc alkoxides, SnO, PbO, Sn (2-ethyl hexanoates), Sb (2-ethyl hexanoates), Bi (2-ethyl hexanoates), Na (2-ethyl hexanoates) (sometimes called octoates), Ca stearates, Mg stearates, Zn stearates, and tetraphenyltin. Applicants have also tested several catalysts for polymerization of lactide at 180° C. which include: tin(II) bis(2-ethyl hexanoate) (commercially available from Atochem, as Fascat 2003, and Air Products as DABCO T-9), dibutyltin diacetate (Fascat 4200®, Atochem), butyltin tris(2-ethyl hexanoate) (Fascat 9102®, Atochem), hydrated monobutyltin oxide (Fascat 9100®, Atochem), antimony triacetate (S-21, Atochem), and antimony tris(ethylene glycoxide) (S-24, Atochem). Of these catalysts, tin(II) bis(2-ethyl hexanoate), butyltin tris (2-ethyl hexanoate) and dibutyltin diacetate appear to be most effective.

Applicants have found the use of catalysts to polymerize lactide significantly affects the stability of the resin product. It appears the catalyst as incorporated into the polymer also is effective at catalyzing the reverse depolymerization reaction. Example 10 details the effect of residual catalyst on degradation. To minimize this negative effect, in a preferred composition, the residual catalyst level in the resin is present in a molar ratio of initial monomer-to-catalyst greater than about 3,000:1, preferably greater than about 5,000:1 and most preferably greater than about 10,000:1. Applicants believe a ratio of about 20,000:1 may be used, but polymerization will be slow. Optimization of catalyst levels and the benefits associated therewith are detailed in Example 20. Applicants have found that when the catalyst level is controlled within these parameters, catalytic activity is sufficient to polymerize the lactide while sufficiently low to enable melt-processing without adverse effect when coupled with low residual monomer level and low water concentration as described above in polymers of molecular weight between 10,000 to about 200,000. It is believed in most applications the addition of a stabilizing agent may be unnecessary if catalyst level is optimized.

Applicants have also found that catalyst concentration may be reduced subsequent to polymerization by precipitation from a solvent. Example 21 demonstrates potential catalyst removal by precipitation from a solvent. This produces a resin with reduced catalyst concentration. In an alternative embodiment, the catalyst means for catalyzing the polymerization of lactide to form the poly(lactide) polymer chains which was incorporated into the melt-stable lactide polymer composition during polymerization is deactivated by including in the melt-stable lactide polymer composition a catalyst deactivating agent in amounts sufficient to reduce catalytic depolymerization of the poly (lactide) polymer chains. Example 11 details the benefits of utilizing a catalyst deactivating agent. Such catalyst-deactivating agents include hindered, alkyl, aryl and phenolic hydrazides, amides of aliphatic and aromatic mono- and dicarboxylic acids, cyclic amides, hydrazones and bishydrazones of aliphatic and aromatic aldehydes, hydrazides of aliphatic and aromatic mono- and dicarboxylic acids, bis-acylated hydrazine derivatives, and heterocyclic compounds. A preferred metal deactivator is Irganox® MD1024 from Ciba-Geigy. Biodegradable metal deactivators are particularly preferred.

In an alternative embodiment, the catalyst concentration is reduced to near zero by utilizing a solid-supported catalyst to polymerize lactide. The feasibility of utilizing such catalyst is detailed in Example 8. It is believed catalysts which may be utilized include supported metal catalysts, solid acid catalysts, acid clays, alumina silicates, alumina, silica and mixtures thereof.

In a preferred composition, the catalyst usage and/or deactivation is controlled to reduce depolymerization of the poly(lactide) polymer during melt-processing to less than about 2 percent by weight generation of lactide from a devolatilized sample in the first hour at 180° C. and atmospheric pressure. More preferably, the amount of lactide generated is less than about 1 percent by weight in the first hour and most preferably less than about 0.5 percent by weight in the first hour.

A preferred melt-stable lactide polymer composition is the reaction product of polymerization of lactide at a temperature greater than about 160° C. Applicants have found that polymerization at higher temperatures result in a characteristically different polymer which is believed to have improved melt stability due to increased transesterification during polymerization. The benefits of higher temperature polymerization are detailed in Example 12.

Melt-Stable Lactide Polymer Process

The process for the manufacture of a melt-stable lactide polymer comprises the steps of first providing a lactide mixture wherein the mixture contains about 5 percent by weight to about 50 percent by weight meso-lactide and about 95 percent by weight or less L-lactide and/or D-lactide. Such purified lactide stream may be such as that produced in the process disclosed by Gruber et al., although the source of lactide is not critical to the process of the present invention.

The lactide mixture is polymerized to form a lactide polymer or poly(lactide) with some residual unreacted monomer in the presence of a catalyst means for catalyzing the polymerization of lactide to form poly(lactide). Catalysts suitable for such polymerization have been listed previously. The concentration of catalysts utilized may be optimized as detailed in the following examples and discussed previously.

In a preferred embodiment, a stabilizing agent, which may be an antioxidant and/or a water scavenger is added to the lactide polymer. It is recognized that such stabilizing agents may be added simultaneously with or prior to the polymerization of the lactide to form the lactide polymer. The stabilizing agent may also be added subsequent to polymerization.

As previously disclosed, the catalyst usage is adjusted and/or deactivation agent is added in a sufficient amount to reduce depolymerization of poly(lactide) during melt-processing to less than 2 percent by weight generation of lactide from a devolatilized sample in the first hour at 180° C. and atmospheric pressure. More preferably, the stabilizing agent controls lactide generation to less than 1 percent by weight and most preferably less than 0.5 percent by weight in the first hour at 180° C. and atmospheric pressure. Alternatively, the control of catalyst concentration to optimize the balance between necessary catalytic activity to produce poly(lactide) versus the detrimental effects of catalytic depolymerization or degradation of the lactide polymer may be utilized to obviate the need for adding a stabilizing agent.

The lactide polymer is then devolatilized to remove unreacted monomer which may also be a by-product of decomposition reactions or the equilibrium-driven depolymerization of poly(lactide). Any residual water which may be present in the polymer would also be removed during devolatilization, although it is recognized that a separate drying step may be utilized to reduce the water concentration to less than about 2,000 parts-per-million. The devolatilization of the lactide polymer may take place in any known devolatilization process. The key to selection of a process is operation at an elevated temperature and usually under conditions of vacuum to allow separation of the volatile components from the polymer. Such processes include a stirred tank devolatilization or a melt-extrusion process which includes a devolatilization chamber and the like. An inert gas sweep is useful for improved devolatization.

In a preferred process for manufacture of a melt-stable lactide polymer composition, the process also includes the step of adding a molecular weight control agent to the lactide prior to catalyzing the polymerization of the lactide. For example, molecular weight control agents include active hydrogen-bearing compounds, such as lactic acid, esters of lactic acid, alcohols, amines, glycols, diols and triols which function as chain-initiating agents. Such molecular weight control agents are added in sufficient quantity to control the number average molecular weight of the poly(lactide) to between about 10,000 and about 200,000.

Next referring to FIG. 1 which illustrates a preferred process for producing a melt-stable lactide polymer composition. A mixture of lactides enters mixing vessel (3) through a pipeline (1). A catalyst for polymerizing lactide is also added through a pipeline (13). Within mixing vessel (3) a stabilizing agent may be added through a pipeline (2). A water scavenger may also be added through the pipeline (2). The stabilized lactide mixture is fed through a pipeline (4) to a polymerization process (5). The polymerized lactide or lactide polymer leaves the polymerization process through a pipeline (6). The stream is fed to a second mixing vessel (8)

within which a stabilizing agent and/or catalyst deactivating agent may be added through a pipeline (7). The stabilized lactide polymer composition is then fed to a devolatilization process (10) through a pipeline (9). Volatile components leave the devolatilization process through a pipeline (11) and the devolatilized lactide polymer composition leaves the devolatilization process (10) in a pipeline (12). The devolatilized lactide composition is fed to a resin-finishing process (14). Within the resin-finishing process the polymer is solidified and processed to form a pelletized or granular resin or bead. Applicants recognize the polymer may be solidified and processed to form resin or bead first, followed by devolatilization. The resin is then fed to a drying process (16) conveyance means (15). Within the drying process (16) moisture is removed as a vapor through pipeline (17). The dried lactide polymer resin leaves the drying process (16) by a conveyance means (18) and is fed to a melt-processing apparatus (19). Within the melt-processing apparatus (19) the resin is converted to a useful article as disclosed above. The useful article leaves the melt-processing apparatus (19) through a conveyance means (20).

A typical method of coating paper is by extruding a melt through a die onto a moving substrate. The method of coating for the present invention is not limited and includes all known methods of applying a coating to paper. After the coating process, the paper may be calendared to improve surface properties such as smoothness and glossy. In the calendaring process, the coated paper passes through alternating hard and soft rolls which reform the surface, often producing a gloss while smoothing or leveling surface face contours.

The following examples further detail advantages of the system disclosed herein:

EXAMPLE 1

Paper with a high gloss, water resistant, biodegradable coating.

A 20 percent solution of poly(lactide) with a molecular weight of 40,000 in a solvent of chloroform was cast onto 50 lb kraft paper (Georgia Pacific) using a 15 mil draw bar. After allowing the coating to dry at room temperature for 24 hours, the coated paper was placed into a vacuum oven at 40° C. and high vacuum for 24 hours to remove the residual solvent. Coating thickness after drying was 2 mils. The resultant coating had excellent clarity and high gloss; a 60° gloss value of 83 was found according to ASTM D 523-85. Exposing the coating to water for 8 hours did not affect its appearance. The flexibility of the coating was verified by bending the coating over a ⅛" mandrel.

EXAMPLE 2

Heat sealability of a biodegradable paper coating.

A 20 percent poly(lactide) in chloroform solution was cast onto 50 lb kraft paper (George Pacific) using a 15 mil and a 25 mil draw bar. The coated paper was allowed to dry at room temperature for 24 hours. Residual solvent was removed in a vacuum oven at 30° C. under high vacuum. The dried coating thicknesses were 2 mil and 4 mil respectively.

The coated paper was tested for its heat sealability to uncoated paper using 1" wide test specimen. A Sencorp Heat Sealer Model 12-As/1 was used to apply a preset pressure for a given time and temperature with two 1×12" jaws. The 1" wide coated paper was mated to an uncoated paper of the same dimensions. The pressure was varied from 60 to 80 psi, the temperature from 200° to 280° F., and the time from 0.5 to 1.5 seconds. The samples were allowed to cool to room temperature. The quality of the resultant bond was thereafter assessed using a hand T-peel test and visually judging the degree of fiber tear from the substrates.

Samples were judged an "excellent" heat seal (2) if they had 100 percent fiber tear of the uncoated strip onto the coating. A "better" heat seal (1) was partial fiber tear of the uncoated strip. "Poor" heat seal (0) indicates no fiber tear. The tests were run using both a 2 mil and 4 mil coating. An * indicates an average of multiple tests. The following are the results:

TABLE 1

| Time (Sec) | | | | | | | | | |
|---|---|---|---|---|---|---|---|---|---|
| 1.5 | 0 | 0 | 1 |   | 2 | 2 |   |   |   |
| 1.0 | 0 |   |   | 1 | 1 | 1* | 2* | 2* |   |
| 0.5 | 0 |   | 0 | 0 | 0 | 0* | 0* | 1.5* |   |
|   | 220 | 210 | 220 | 230 | 240 | 250 | 260 | 270 | 280 |
|   | | | | TEMPERATURE °(F.) | | | | | |

0 = POOR 1 32 BETTER 2 = EXCELLENT
* = AVERAGE OF MULTIPLE TESTS

Due to the thermoplastic nature of the coating, the bonded substrates may be debonded upon application of heat and stress at the bondline as the coating softens. This offers an additional option for recycling of coated paper.

EXAMPLE 3

Repulpability of the biodegradable coating at pH 7.

A 20 percent solution of poly(lactide) in chloroform was cast onto 70 lb kraft paper (Georgia Pacific) and dried overnight at room temperature. The residual solvent was removed in a vacuum oven at 30° C. under high vacuum. The dry coating thickness was 5 mil.

Several one square inch pieces of the coated paper were placed in one liter of pH 7, 140° F. water in a Waring blender. The solids content was 2 percent w/v. The coated paper was mixed at a low shear setting for 8 minutes. The coating was removed from the pulp by filtering through a No. 5 sieve. Although a small amount of fiber remained adhered to the coating, the compostability of such mixture would be excellent. Also, recoverability of the lactic acid from the hydrolysis of the coating would not be hindered by the presence of trace levels of wood fiber.

EXAMPLE 4

Repulpability of the biodegradable coating under alkaline conditions.

One square inch pieces of the coated paper prepared in Example 3 were placed into 1 liter of pH 10 water at 140° F. in a Waring blender. The solids content was 2 percent w/v. After agitating for 8 minutes at a low shear setting, the fibers were recovered by filtering through a No. 5 sieve. Although a small amount of fiber remained adhered to the coating, the compostability of such a mixture would be excellent. Also, recoverability of the lactic acid from the hydrolysis of the coating would not be hindered by the presence of the trace levels of wood fiber.

EXAMPLE 5

Surface Energy

Using solutions of varying surface tension from 40 to 50 dynes/cm, the poly(lactide) surface energy was assessed.

Each solution was applied (using a cotton tipped swab) to the surface of a poly(lactide) coated kraft paper. The solutions which wetted the surface were lower than 44 dynes/cm. The solutions of about 44 dynes/cm and greater beaded up on the surface within 2 seconds. Therefore, the surface energy of poly(lactide) is about 44 dynes/cm. This is similar to the surface modified polyethylene which has been modified for adhesion to paper and for printing.

EXAMPLE 6

Lactide Fouling of Process Equipment

Two samples of dried and devolatilized polylactide were melt-processed using a Killion 1" diameter extruder, L/D= 3011, 3:1 compression, with a 6" sheet die. Die temperature was 150° C. and the roll stack temperature was 38° C. Sheet thickness was 0.015 inch.

Sample 1 had a lactide content of 1.1 percent. During processing, fumes were seen between the die and top roll. Lactide began building up on the roll instantly. After 20 minutes the top roll was white with lactide. Also, defects such as pitting were found in the sheet.

Sample 2 had a lactide content of 0.2 percent. No fumes were observed during processing. After 45 minutes of running there was still significantly less lactide buildup than was observed after 20 minutes for sample 1.

This example demonstrates the benefit of a low residual lactide content in preventing fouling of process equipment.

EXAMPLE 7

Lactide and Poly(lactide) Equilibrium Concentrations

Experiments were conducted to determine the equilibrium concentration of lactide and poly(lactide) at different temperatures. In these experiments a sample of lactide was polymerized in the presence of a catalyst (tin (II) bis(2-ethyl hexanoate)) and held at a fixed temperature for 18 hours or greater. Beyond this time the residual monomer concentration is believed essentially constant. The content of residual monomer was determined by GPC analysis. GPC analysis was conducted with an Ultrastyragel® column from Waters Chromatography. The mobile phase was chloroform. A refractive index detector with molecular weight calibration using polystyrene standards was used. The GPC temperature was 35° C. Data analysis was completed using the software package Baseline, model 810, version 3.31.

Figure 2:
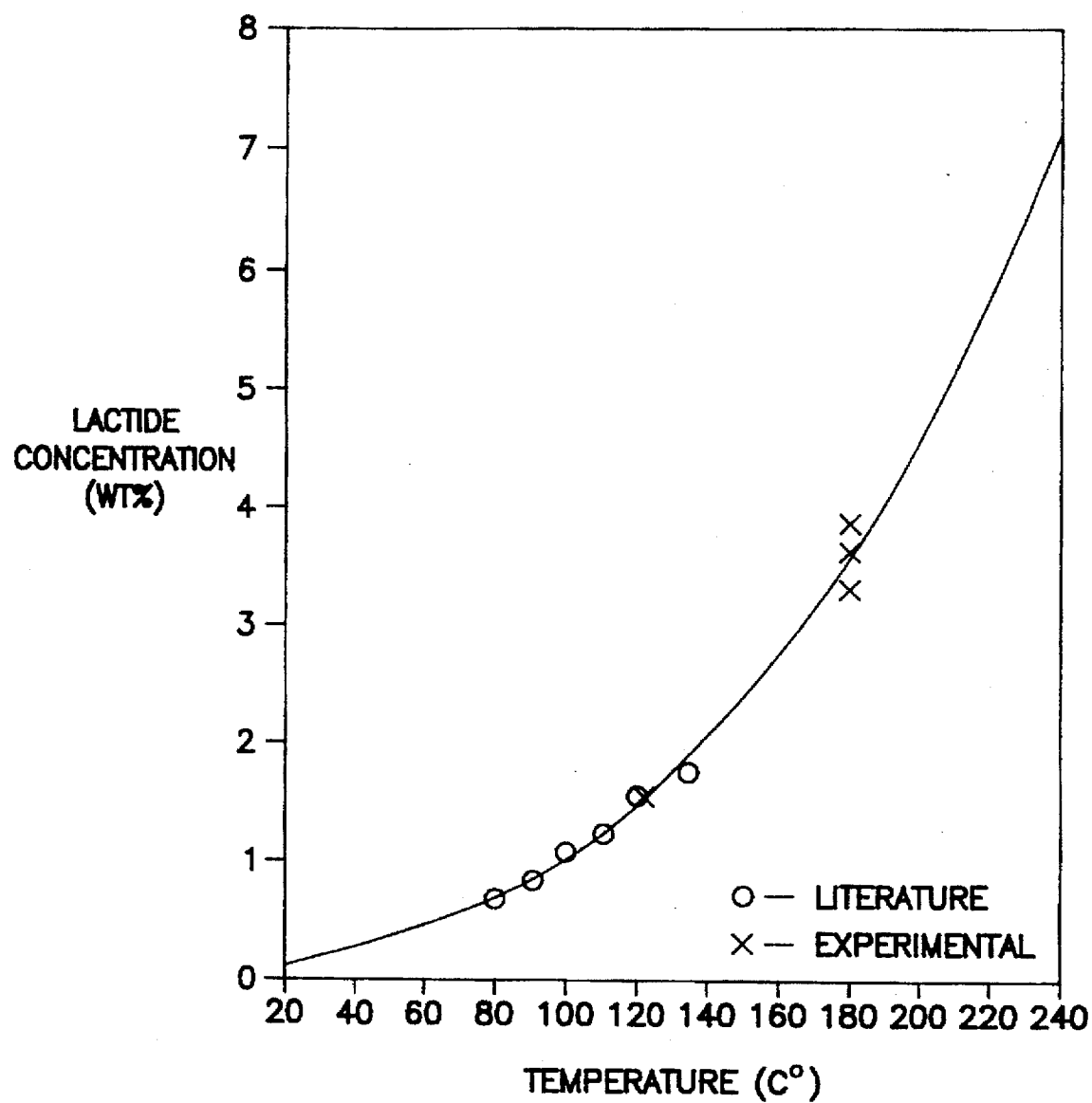
FIG. 2 is a graph showing the equilibrium relationship between lactide and poly(lactide) at various temperatures.

The results of tests conducted on several samples at various temperatures are summarized in the graph of FIG. 2 as indicated by X's on such graph. Also plotted on the graph of FIG. 2 are data points cited in A. Duda and S. Penczek, *Macromolecules*, vol. 23, pp. 1636–1639 (1990) as indicated by circles on the graph. As can be seen from the graph of FIG. 2, the equilibrium concentration, and thus the driving force behind the depolymerization of poly(lactide) to form lactide, increases dramatically with increased temperature. Thus, melt-processing at elevated temperatures results in degradation of the lactide polymer to form lactide on the basis of equilibrium alone. For example, lactide concentrations below about 2 percent cannot be directly obtained at temperatures of 140° C. or above due to the identified equilibrium relationship between lactide and poly(lactide).

EXAMPLE 8

Lactide Polymerization in the Presence of a Solid Supported Catalyst

Tin (II) Oxide 24 grams of L-lactide (melting point about 97° C.) and 6 grams of D,L-lactide (for the purposes of this invention, D,L-lactide has a melting point of about 126° C.) were combined in a round bottom flask with 0.033 grams of Tin (II) oxide, as a fine powder. This corresponds to the catalyst level of 852:1, molar ratio lactide to tin. The flask was then purged with dry nitrogen 5 times. This was lowered into an oil bath at 160° C. with magnetic stirring. Polymerization time was 8 hours.
Amberlyst 36

24 grams of L-lactide and 6 grams of D,L-lactide were combined in a round bottom flask with 1.06 grams of Amberlyst 36 resin beads. The flask was purged 5 times with dry nitrogen. The flask was lowered into an oil bath at 140° C. with magnetic stirring. Polymerization time was 8 hours. The resin had a stated proton content of 1 meq/gram dry weight resin. The resin was prepared by rinsing 2 times with 10 volumes dry methanol, then dried for several hours under high vacuum for several hours at 40° C.

The polymerization results are shown below:

TABLE 2

| Sample | Mn | Mv | PDI | I Conversion |
| --- | --- | --- | --- | --- |
| Tin (II) Oxide | 77,228 | 103,161 | 1.34 | 54.0 |
| Amberlyst | 1,112 | 1,498 | 1.34 | 73.5 |

EXAMPLE 9

Molecular Weight Relationship to Physical Properties of Lactide Polymers

Poly(lactide) samples with various molecular weights and optical compositions were prepared by polymerizing blends of L-lactide and meso-lactide at 180° C. under nitrogen in a 1-gallon sealed reactor. Tin(II) bis(2-ethyl hexanoate) catalyst was added at a monomer-to-catalyst ratio of 10,000:1. After about 1 hour the molten polymer was drained from the reactor using nitrogen pressure. The sample was poured into a pan and placed in a vacuum oven at about 160° C. for about 4 hours to bring the reaction to near equilibrium levels.

Portions of the samples were then dried under vacuum and processed in an injection molding apparatus (New Britain 75 from New Britain Machine Co.) to produce standard test bars for physical property testing. The results of physical property testing are shown in the following Table 3. The physical property tests were made according to ASTM methods D 638, D 256, and D 790. The reported results are the averages of several tests.

Samples of the test bars after injection molding were analyzed by GPC for molecular weight. Other portions of the test bars were reground and tested in a capillary viscometer to determine the melt-viscosity. These results are also included in Table 3.

Statistical analysis of the data revealed no correlations which were statistically significant between either optical composition or molecular weight and the mechanical properties of modulus, tensile strength, percentage elongation at break, notched Izod impact strength, flexural modulus, or flexural strength. The independence of these properties on molecular weight indicates that all of these samples were above a "threshold" molecular weight required to achieve the intrinsic properties of the polymer in a preferred composition.

The viscosity data show significant correlations with molecular weight. This dependence documents the practical limitation and necessity of controlling polymer molecular weight below an upper limit at which it is impractical to melt-process the polymer. At high molecular weight, high viscosity prevents processing by standard melt-processing equipment. Increases in temperature to reduce viscosity dramatically increase polymer degradation and lactide formation which is also unacceptable.

TABLE 3

| Sample I.D. | Meso Lactide In Blend, Wt % | Molecular Weight After Injection Weight | Viscosity at 173° C. (Pa · S) | | |
|---|---|---|---|---|---|
| | | | Final IV (dl/g) | Shear Rate 100 S$^{-1}$ | Shear Rate 1000 S$^{-1}$ |
| 6 | 40 | 41000 | 0.86 | 5.5 | 2.9 |
| 5 | 10 | 54000 | 0.88 | 10.4 | 7.2 |
| 4 | 20 | 59000 | 0.91 | 10.4 | 7.2 |
| 8 | 10 | 64000 | 1.02 | 15.7 | 10.0 |
| 9 | 40 | 68000 | 0.97 | 12.6 | 8.1 |
| 7 | 20 | 71000 | 1.16 | 36.0 | 12.9 |
| 10 | 20 | 83000 | 1.19 | 35.8 | 15.8 |

| Mechanical Properties of Injection Molded Samples | | | | | | |
|---|---|---|---|---|---|---|
| Sample I.D. | Modulus MPSI | Tensile Strength (Yld) PSI | % Elongation at Break | IZOD Impact ft · lb./in | Flexural Modulus MPSI | Flexural Strength PSI |
| 6 | 0.55 | 6600 | 3.3 | 0.39 | 0.53 | 11300 |
| 5 | 0.56 | 7800 | 3.5 | 0.46 | 0.34 | 12500 |
| 4 | 0.56 | 7600 | 3.9 | 0.32 | 0.53 | 12500 |
| 8 | 0.55 | 7700 | 3.4 | 0.47 | 0.53 | 12400 |
| 9 | 0.59 | 6700 | 3.1 | 0.42 | 0.52 | 10600 |
| 7 | 0.56 | 7400 | 3.3 | 0.45 | 0.51 | 12400 |
| 10 | 0.55 | 6700 | 3.0 | 0.47 | 0.52 | 9900 |

EXAMPLE 10

Effect of Residual Catalyst on Polymer Degradation

Polymer samples were prepared at four levels of catalyst, corresponding to monomer to catalyst molar ratios of 5,000:1, 10,000:1, 20,000:1, and 40,000:1. The catalyst utilized was tin (II) bis(2-ethyl hexanoate). These samples were then subjected to heating in a TGA apparatus (TA Instruments, Inc., model 951 thermogravometric analyzer with a DuPont 9900 computer support system) with a nitrogen purge. Isothermal conditions of 200° C. for 20 minutes were used. The samples were then analyzed by GPC with a viscosity-based detector and a universal calibration curve to determine the extent of breakdown in molecular weight. The GPC apparatus for this test was a Viscotek Model 200 GPC and a Phenomenex column. The TGA analysis typically resulted in about a 5 percent loss in weight and molecular weight drops of 0 to 70 percent.

The number average molecular weights were converted to a milliequivalent per kilogram basis (1,000,000/Mn) in order to calculate a rate of chain scission events. The results below represent averages of 2-4 replicates on each of the four samples.

TABLE 4

| Catalyst level (monomer/catalyst) | Scission Rate (meg/kg*min) |
|---|---|
| 5,000 | 1.33 |
| 10,000 | 0.62 |
| 20,000 | 0.44 |
| 40,000 | 0.12 |

The rate of chain scission was directly proportional to the residual catalyst level, demonstrating the detrimental effect of catalyst activity on melt-stability under conditions similar to melt-processing. This instability, however, is distinguished from the instability due to the equilibrium relationship between lactide and poly(lactide) detailed in Example 7, in that loss of molecular weight due to catalytic depolymerization by chain scission is evident.

EXAMPLE 11

Catalyst Deactivation Experiment

Two runs were made in a laboratory Parr reactor. Lactide feed was 80 percent L-lactide and 20 percent D,L-lactide. Molecular weight was controlled by adding a small quantity of lactic acid, the target molecular weight was 80,000 Mn.

Lactide was charged to the reactor as a dry mix, the reactor was purged 5 times with nitrogen, and heated up to 180° C. At this point catalyst (5000:1 initial monomer to catalyst molar ratio, Fascat® 2003) was charged through a port in the top of the reactor. The reaction was allowed to proceed for 70 minutes at 180° C., with mechanical agitation. Conversion at this point was 93–94 percent, close to the equilibrium value at 180° C. of 96 percent poly(lactide) from FIG. 2. This point is considered t-zero, designating the completion of the polymerization reaction and the beginning of the mixing time.

In the control experiment, a sample was taken and the mixture was held at temperature with continued agitation.

Samples were taken periodically through a port in the reactor bottom. After 4 hours the reactor was drained.

In the example experiment, a sample was taken and 0.25 weight percent of a metal deactivator (Irganox® MD 1024®) was added through the catalyst addition port. The mixture was held at temperature with continued agitation and samples were withdrawn periodically. The reactor was drained after 4 hours.

GPC analysis (utilizing the method of Example 7) for these samples was divided into three parts: polymer with molecular weight over 4,000 (for which the Mn and Mw numbers are reported), the percent oligomers (comprising the region with molecular weight greater than lactide but less than 4,000, as distinguished from oligomers as defined by Loomis to include only oligomers up to a molecular weight of 450), and percent lactide (residual monomer). The structure of the oligomers was not certain, but it is believed they were primarily cyclic structures. It is also believed that the metal deactivator, if unreacted, will elute with the oligomer fraction. Quantification of the oligomer fraction is difficult, because the GPC trace is near the baseline in this region.

The analysis of the polymer samples as withdrawn from the reactor at various time intervals for the control and experimental compositions are shown below in Table 5.

TABLE 5

| Control | Mn | Mw | % Polymer | % Oligomer | % Monomer |
| --- | --- | --- | --- | --- | --- |
| t-zero | 67,100 | 119,500 | 94 | 0 | 6.0 |
| 0.5 hr | 62,500 | 119,000 | 95 | 0.7 | 3.9 |
| 1.0 hr | 61,500 | 116,100 | 96 | 0 | 3.6 |
| 1.5 hr | 56,000 | 111,600 | 95 | 1.5 | 3.3 |
| 2.0 hr | 57,600 | 110,900 | 96 | 0.9 | 3.1 |
| 4.0 hr | 51,400 | 105,400 | 94 | 3.3 | 3.1 |

| Test | Mn | Mw | % Polymer | % Oligomer | % Monomer |
| --- | --- | --- | --- | --- | --- |
| t-zero | 63,200 | 110,700 | 93 | 3.5 | 3.8 |
| 0.5 hr | 52,100 | 108,600 | 92 | 4.6 | 2.9 |
| 1.0 hr | 52,700 | 109,200 | 92 | 4.9 | 2.8 |
| 1.5 hr | 53,400 | 107,200 | 93 | 4.0 | 3.1 |
| 2.0 hr | 59,700 | 111,100 | 94 | 0.6 | 5.8 |
| 4.0 hr | 51,200 | 107,300 | 91 | 6.1 | 3.3 |

The samples were then ground and placed in a 120° C. oven under vacuum (pressure 0.1 inch Hg) for 14 hours. Sample analyses after this treatment are shown below in Table 6.

TABLE 6

| Control | Mn | Mw | % Polymer | % Oligomer | % Monomer |
| --- | --- | --- | --- | --- | --- |
| t-zero | 45,500 | 88,500 | 98 | 2.2 | 0.0 |
| 0.5 hr | 45,000 | 88,700 | 98 | 2.0 | 0.0 |
| 1.0 hr | 43,900 | 87,200 | 98 | 2.0 | 0.0 |
| 1.5 hr | 42,600 | 84,000 | 98 | 2.2 | 0.0 |
| 2.0 hr | 42,000 | 85,200 | 97 | 3.2 | 0.0 |
| 4.0 hr | 41,900 | 82,800 | 98 | 2.0 | 0.0 |

| Test | Mn | Mw | % Polymer | % Oligomer | % Monomer |
| --- | --- | --- | --- | --- | --- |
| t-zero | 39,300 | 76,700 | 96 | 4.0 | 0.0 |
| 0.5 hr | 43,900 | 85,100 | 98 | 2.4 | 0.0 |
| 1.0 hr | 55,300 | 98,600 | 96 | 3.8 | 0.0 |
| 1.5 hr | 48,400 | 96,200 | 95 | 4.5 | 0.0 |
| 2.0 hr | 48,900 | 101,900 | 95 | 5.0 | 0.0 |
| 4.0 | 50,600 | 101,900 | 94 | 5.6 | 0.0 |

In all cases the polymer was completely devolatilized (0.0 percent residual lactide monomer). The data also clearly show that the metal deactivator reduced the degradation of polymer during the devolatilization step (as indicated by the greater loss in Mn for the control samples from Table 4 to Table 5 versus the Test samples). One hour of mixing appears to be long enough to develop most of the benefit.

The samples were stored at room temperature under nitrogen for about 1 week and reanalyzed, as shown below in Table 7.

TABLE 7

| Control | Mn | Mw | % Polymer | % Oligomer | % Monomer |
| --- | --- | --- | --- | --- | --- |
| t-zero | 33,500 | 71,000 | 100 | 0.1 | 0.0 |
| 0.5 hr | 43,400 | 95,800 | 99 | 1.0 | 0.0 |
| 1.0 hr | 44,900 | 96,300 | 100 | 0.1 | 0.0 |
| 1.5 hr | 45,900 | 95,000 | 100 | 0.0 | 0.0 |
| 2.0 hr | 45,900 | 94,100 | 100 | 0.2 | 0.0 |
| 4.0 hr | 43,100 | 90,100 | 99 | 1.3 | 0.0 |

| Test | Mn | Mw | % Polymer | % Oligomer | % Monomer |
| --- | --- | --- | --- | --- | --- |
| t-zero | 44,600 | 84,900 | 100 | 0.0 | 0.0 |
| 0.5 hr | 45,300 | 90,600 | 99 | 1.2 | 0.0 |
| 1.0 hr | 47,800 | 100,000 | 98 | 2.4 | 0.0 |
| 1.5 hr | 46,600 | 98,900 | 96 | 3.5 | 0.0 |
| 4.0 | 57,700 | 110,200 | 96 | 4.0 | 0.3 |

Equilibrium lactide levels are estimated to be less than 0.2 weight percent at room temperature. Consistent with that, essentially no lactide was observed in any of the samples (detection limit about 0.1 weight percent). The oligomer content in the non-stabilized samples declined and some increase in molecular weight was noted, perhaps due to reincorporation of the (cyclic) oligomers into the polymer. The oligomer depletion reaction was inhibited in the stabilized polymers, with the extent of inhibition dependent on the length of time that the additive was mixed.

The samples were then reheated to 180° C. in sealed vials and held for one hour as a simulation of melt-processing. Analysis of the samples after the heat treatment is given below in Table 8.

TABLE 8

| Control | Mn | Mw | % Polymer | % Oligomer | % Monomer |
| --- | --- | --- | --- | --- | --- |
| t-zero | 23,900 | 60,000 | 88 | 8.4 | 4.0 |
| 0.5 hr | 23,900 | 59,600 | 90 | 7.7 | 2.7 |
| 1.0 hr | 23,700 | 58,800 | 88 | 9.3 | 2.7 |
| 1.5 hr | 24,700 | 58,000 | 86 | 10.0 | 3.8 |
| 2.0 hr | 26,100 | 56,400 | 90 | 6.8 | 2.7 |
| 4.0 hr | 24,800 | 58,700 | 92 | 6.6 | 1.9 |

| Test | Mn | Mw | % Polymer | % Oligomer | % Monomer |
| --- | --- | --- | --- | --- | --- |
| t-zero | 33,900 | 64,300 | 95 | 2.2 | 3.1 |
| 0.5 hr | 17,900 | 34,600 | 94 | 4.8 | 1.7 |
| 1.0 hr | 21,200 | 42,900 | 94 | 4.6 | 1.8 |
| 1.5 hr | 29,200 | 56,900 | 98 | 0.5 | 1.8 |
| 2.0 hr | missing | | | | |
| 4.0 hr | 35,700 | 71,400 | 95 | 3.7 | 1.7 |

The data for molecular weight show that if the metal deactivator is not mixed into the system long enough then it can have a detrimental impact on stability in the melt. The samples for which the mixing was at least 1.5 hours show no detrimental effect, and the 4 hour sample appears to be somewhat more stable than any of the others based on molecular weight alone. More importantly, the metal deactivator samples show significantly less lactide reformation than the control samples. This effect is gained even in the samples which were mixed for only 0.5 hour. The metals deactivated samples averaged only 1.8 percent lactide after one hour at 180° C., compared to an average of 3.0 percent lactide for the controls. The equilibrium level at 180° C. is about 3.6 percent from FIG. 2. Thus, the use of metal deactivators can reduce the troublesome reformation of lactide during melt-processing of the finished polymer.

EXAMPLE 12

Effect of Increased Polymerization Temperature On Polymer Characteristics

L-lactide (Boeringer Ingleheim, S-grade) was used as received, meso-lactide (PURAC) was purified by distillation to remove traces of D- and L-lactide. The melting point of the purified meso-lactide was 54° C. Lactide mixtures were made up to the following ratios: 100 percent L-lactide, 90/10 L-lactide/meso-lactide, 70/30 L-lactide/meso-lactide, 50/50 L-lactide/meso-lactide, and 100 percent meso-lactide. Catalyst level was 2,500:1 molar ratio of initial monomer to tin with the tin being tin(II) bis(2-ethyl hexanoate) (Fascat® 9002). Lactic acid was added as a molecular weight control agent to target a number average molecular weight of 50,000 (the same amount was added to all samples). Polymerization times were estimated to obtain conversions of 50 percent and 90 percent. For 120° C. this was 4 hours and 16 hours, respectively. For 180° C. these times were 10 minutes and 50 minutes, respectively. Below in Table 9 are the GPC results (method of Example 7) of tests on the polymer samples produced by this procedure.

TABLE 9

| L/meso | Temp | Mn | Mw | PDI | % Conv |
|---|---|---|---|---|---|
| 100% L | 120° C. | 31,014 | 33,774 | 1.09 | 53.2 |
|  |  | 45,864 | 52,574 | 1.15 | 87.1 |
| 100% L | 180° C. | 27,785 | 32,432 | 1.17 | 46.7 |
|  |  | 56,839 | 98,125 | 1.73 | 93.3 |
| 90/10 | 120° C. | 34,541 | 38,586 | 1.12 | 62.3 |
|  |  | 29,222 | 34,466 | 1.18 | 89.3 |
| 90/10 | 180° C. | 31,632 | 35,713 | 1.13 | 48.5 |
|  |  | 57,925 | 110,841 | 1.91 | 94.8 |
| 70/30 | 120° C. | 41,211 | 45,222 | 1.10 | 60.1 |
|  |  | 58,284 | 71,257 | 1.22 | 89.1 |
| 70/30 | 180° C. | 32,292 | 37,401 | 1.16 | 53.8 |
|  |  | 51,245 | 107,698 | 2.10 | 96.5 |
| 50/50 | 120° C. | 15,888 | 17,969 | 1.13 | 57.8 |
|  |  | 25,539 | 31,834 | 1.25 | 90.6 |
| 50/50 | 180° C. | 34,375 | 42,018 | 1.22 | 62.5 |
|  |  | 44,590 | 98,028 | 2.20 | 95.5 |
| 100% meso | 120° C. | 33,571 | 40,635 | 1.21 | 73.4 |
|  |  | 45,237 | 68,142 | 1.51 | 94.3 |
| 100% meso | 180° C. | 30,976 | 42,987 | 1.39 | 67.6 |
|  |  | 40,038 | 83,815 | 2.09 | 96.6 |

The results show that the ultimate number average molecular weight was not significantly affected by the temperature of polymerization, with an average of 41,000 at 120° C. and 50,000 at 180° C. This implies that each lactic acid molecule initiates about one polymer chain, regardless of temperature. The ultimate weight average molecular weight is, however, significantly affected by temperature. At 120° C. the weight average molecular weight averaged 52,000 and at 180° C. the average was 100,000. This is believed to be due to a relative increase in the rate of transesterification at 180° C. The polydispersity index (PDI) at high conversion also reflects this, averaging 1.3 at 120° C. and 2.0 at 180° C. It is believed these differences would have a significant effect on the melt-processing characteristics of the polymer, with the higher weight average molecular weight of the polymer produced at 180° C. expected to translate into better melt strength and processability.

These experiments show that polymerization at a higher temperature results in a polymer that is characteristically different. Further, the glass transition temperature for the samples polymerized at higher temperature is higher.

EXAMPLE 13

Experiments with Stabilizing Agents and Metal Deactivators

Test 1

Conditions: vial polymerization, (Lactide is melted under a nitrogen-purged atmosphere in a round bottom flask with stirring. Catalyst and additives are added and aliquots of the mixtures are pipetted into silanized glass vials. Typically 5–10 grams of reaction mixture are used in a 16 ml. vial. The vials are tightly capped and placed into a preheated oil bath.) 10,000:1 molar ratio of lactide-to-tin, tin(II) bis(2-ethyl hexanoate) catalyst, 0.2 wt percent Ultranox®626 in tetrahydrofuran (THF). 180° C. Time was 90 minutes.

The control with tin only polymerized to 84 percent conversion and reached a MWn of 31,700. The example with tin and Ultranox® polymerized to 83 percent conversion and reached a number average molecular weight (MWn) of 39,800; an increase of 26 percent over the control.

The control sample turned light yellow, the sample with stabilizer remained colorless.

Test 2

Conditions: vial polymerization, 5000:1 molar ratio of lactide to tin, tin(II) bis(2-ethyl hexanoate) catalyst, 0.25 wt percent Ultranox®626 (in THF). 180° C. Time was 60 minutes. Lactide was used from the above described Gruber et al. process.

The control with tin alone polymerized to 67 percent conversion and reached a MWn of 62,900. The example with tin and Ultranox® polymerized to 66 percent conversion and reached a MWn of 75800; an increase of 21 percent over the control.

A second example with tin(II) bis(2-ethyl hexanoate), Ultranox®, and 0.50 percent of Irganox® 1076, which is a phenolic antioxidant, polymerized to 66 percent conversion and reached a number average molecular weight (MWn) of 74500; an increase of 18 percent over the control.

All samples were a dark yellow color, although the samples with stabilizer had a slightly lower absorbance at 300 nm.

Test 3

Conditions: vial polymerization, 10,000:1 molar ratio of lactide to tin, tin(II) bis(2-ethyl hexanoate) catalyst, 180° C., 80 percent L-lactide and 20 percent D,L-lactide purchased from Henley and Aldrich, respectively. Lactic acid was added to control molecular weight to about 75,000 at full conversion. One sample included 0.25 percent Ultranox® 626 phosphite stabilizer, one included 0.25 percent Irganox® 1076 antioxidant, and one control sample.

Samples were taken at various times and analyzed by GPC for conversion and molecular weight (the method of Example 7). The results are summarized in Table 9 below.

TABLE 10

| Time | Control | | Irganox ® | | Ultranox ® | |
|---|---|---|---|---|---|---|
| (hrs) | Mn | % conv | Mn | % conv | Mn | % conv |
| 1 | 31,000 | 46 | 35,900 | 41 | 66,500 | 61 |
| 2 | 45,400 | 74 | 56,800 | 74 | 102,700 | 83 |

TABLE 10-continued

| Time | Control | | Irganox® | | Ultranox® | |
|---|---|---|---|---|---|---|
| (hrs) | Mn | % conv | Mn | % conv | Mn | % conv |
| 4 | 69,600 | 93 | 74,100 | 93 | 97,200 | 91 |
| 11 | 52,900 | 95 | 60,700 | 95 | 71,500 | 94 |

The sample with phosphite stabilizer polymerized faster, shown by the higher conversion at 1 and 2 hours, and went to a higher molecular weight than the control or the sample with Irganox®. The phosphite stabilized sample had a molecular weight more than 30 percent higher than the control for all time periods.

Test 4

The experiment above was repeated to compare the control to the phosphite-stabilized polymer, as summarized in Table 11 below.

TABLE 11

| Time | Control | | Ultranox® | |
|---|---|---|---|---|
| (hrs) | Mn | % conv | Mn | % conv |
| 1 | 36,600 | 37 | 71,500 | 59 |
| 2 | 51,700 | 70 | 95,200 | 85 |
| 4 | 64,400 | 91 | 103,700 | 94 |
| 8 | 58,100 | 96 | 95,700 | 94 |

The sample with phosphite stabilizer again polymerized faster and went to a higher molecular weight than the non-stabilized sample. The phosphite stabilized sample had a molecular weight more than 60% higher than the control for all time periods.

Test 5

Conditions: vial polymerization, 5,000:1 molar ratio of lactide to tin, tin(II) bis(2-ethyl hexanoate) catalyst, 180° C., 80 percent L-lactide and 20 percent D,L-lactide purchased from Henley and Aldrich. Lactic acid was added to control number average molecular weight to an estimated 80,000 at full conversion. One sample was run with 0.25 percent Ultranox® 626 phosphite stabilizer, one with 0.25 percent Irganox® 1076 antioxidant, and one control sample.

Samples taken at various times and analyzed by GPC (the method of Example 1) for conversion and molecular weight. The results are tabulated in Table 12 below.

TABLE 12

| Time | Control | | Irganox® | | Ultranox® | |
|---|---|---|---|---|---|---|
| (hrs) | Mn | % conv | Mn | % conv | Mn | % conv |
| 1 | 83,600 | 76 | 121,900 | 83 | 162,300 | 87 |
| 4 | 74,400 | 93 | 104,300 | 95 | 123,900 | 96 |
| 24 | 40,200 | 96 | 52,000 | 96 | 96,900 | 97 |
| 48 | 34,200 | 97 | 30,400 | 96 | 56,500 | 96 |
| 72 | 25,000 | 96 | 22,400 | 96 | 69,500 | 96 |

The phosphite-stabilized sample had a molecular weight more than 60 percent higher than the control for all time periods. After 72 hours it had a molecular weight 2.8 times higher than the control. The sample with antioxidant showed an initial increase in molecular weight, relative to the control, but the effect disappeared after 48 hours.

The phosphite stabilized sample was significantly lighter in color than the control or the antioxidant treated sample.

Test 6

Conditions: vial polymerization, 5000:1 molar ratio of lactide to tin, tin(II) bis(2-ethyl hexanoate) catalyst, 0.25 wt percent Ultranox® 626 (in THF). 180° C. Time was two hours. Gruber et al. process lactide washed with isopropyl alcohol was used.

The control with tin alone polymerized to 95 percent conversion and reached a number average molecular weight of 118,000. The example with tin and Ultranox® polymerized to 93 percent conversion and reached a number average molecular weight of 151,000, an increase of 28 percent over the control.

Test 7

Conditions: vial polymerization at 180° C. 5000:1 molar ratio of lactide to tin, tin(II) bis(2-ethyl hexanoate) catalyst. Lactide was 80 percent L-lactide and 20 percent D,L-lactide, purchased from Henley and from Aldrich. Lactic acid was added to target the molecular weight to an Mn of 80,000. All stabilizers were added at 0.25 weight percent. Molecular weight (number average) was determined for samples pulled at 3 hours, while rate constants were based on samples pulled at 1 hour. The results of these screening tests on many stabilizing agents following the above procedure are detailed below in Table 13. Product designations in Table 13 are tradenames or registered trademarks.

TABLE 13

| Sample | MWn | % Conversion | Relative Rate |
|---|---|---|---|
| Control 1 | 65,000 | 95.9 | 90 |
| Control 2 | 85,000 | 95.9 | 100 |
| Control 3 | 76,000 | 96.6 | 100 |
| Control 4 | 69,000 | 96.2 | 100 |
| Control 5 | 74,000 | 96.8 | 110 |
| Control 6 | 70,000 | 97.2 | 110 |
| PHOSPHITES | | | |
| Ultranox 626 (GE) | 103,000 | 96.8 | 100 |
| Weston TDP (GE) | 64,000 | 70.0 | 60 |
| Weston PDDP (GE) | 67,000 | 76.7 | 60 |
| Weston PNPG (GE) | 92,000 | 94.1 | 100 |
| Irgafos 168 (Ciba-Geigy) | 95,000 | 95.3 | 120 |
| Weston 618 (GE) | 99,000 | 95.1 | 100 |
| Sandostab P-EPQ (Sandoz) | 108,000 | 94.7 | 110 |
| Weston TNPP (GE) | 88,000 | 97.9 | 130 |
| PHENOLIC ANTIOXIDANTS | | | |
| Irganox 1010 (Ciba-Ceigy) | 95,000 | 97.5 | 110 |
| Cyanox 1790 (Cyanamid) | 98,000 | 96.9 | 120 |
| BHT | 87,000 | 96.5 | 130 |
| Irganox 1076 (Ciba-Ceigy) | 121,000 | 97.8 | 130 |
| Topanol CA (ICI) | 84,000 | 96.6 | 160 |
| AMINES | | | |
| Tinuvin 123 (Ciba-Geigy) | 65,000 | 94.8 | 70 |
| Tinuvin 622 (Ciba-Geigy) | 82,000 | 95.7 | 80 |
| Naugard 445 (Uniroyal) | 93,000 | 98.2 | 120 |
| THIOETHER | | | |
| Mark 2140 (Witco) | 77,000 | 97.0 | 120 |
| METAL DEACTIVATORS | | | |
| Irganox MD1024 (Ciba-Geigy) | 34,000 | 65.7 | 10 |
| Naugard XL-1 (Uniroyal) | 91,000 | 95.8 | 110 |

Note, that with a few exceptions, the phosphites and the phenolic antioxidants provide increased molecular weight with no reduction in polymerization rate. Of the amines, only Naugard® 445 provided stabilization without a rate decrease. The metal deactivators are expected to deactivate the catalyst, as was observed for Irganox® MD1024. The Naugard® XL-1 did not accomplish deactivation.

EXAMPLE 14

Polymer Melt Stability as a Function of Moisture Content

Lactide, produced and purified in a continuous Gruber et al. process, was fed at a rate of 3 kg/hr to a continuous polymerization pilot plant. Catalyst was added with a metering pump at the rate of 1 part catalyst to 5000 parts lactide on a molar basis. The reaction system was blanketed with nitrogen. The reactor vessels consist of two continuous stirred tank reactors (CSTR) in series. The first had a 1-gallon capacity and the second had a 5-gallon capacity. The reactors were run 60–80 percent liquid filled and at 170°–180° C. Polymer melt pumps moved the liquid from CSTR 1 to CSTR 2, and from CSTR 2 through a die into a cooling water trough. The polymer strand thus produced was pulled from the trough by a pelletizer and stored as pellets.

The pelletized poly(lactide) was put into a drying hopper and dried at 40° C. under flowing dry air. Samples were pulled after one hour and four hours. These samples were then run through a single screw Brabender® extruder, with a retention time of approximately 3 minutes. Samples were analyzed for moisture by an automatic Karl Fischer apparatus and for molecular weight by GPC (the method of Example 1). The results of these tests are documented in Table 14 below.

TABLE 14

| Sample | Extruder Temperature (C.) | Weight Average Molecular Weight |
|---|---|---|
| Initial | | 63,000 |
| Dried 1 hour | | |
| (1200 ppm $H_2O$) | 137 | 44,000 |
| | 145 | 48,000 |
| | 162 | 35,000 |
| | 179 | 30,000 |
| Dried 4 hours | | |
| 150 ppm $H_2O$) | 140 | 63,000 |
| | 140 | 69,000 |
| | 160 | 65,000 |
| | 178 | 68,000 |

These results show the detrimental effect of water in the lactide polymer resin during melt polymerization and the need to properly dry the poly(lactide) before melt-processing.

EXAMPLE 15

Degradation of Crystalline and Amorphous Poly(lactide)

Two literature references disclose poly(D,L-lactide) to degrade faster than poly(L-lactide), attributing the result to crystallinity of poly(L-lactide). These are: Kulkarni et al., *J. Biomed. Mater. Res.*, vol. 5, pp. 169–181, (1971); Makino et al., *Chem. Pharm. Bull.*, vol. 33, pp. 1195–1201, (1985). An experiment was conducted to measure the effect of crystallinity on polymer degradation and is detailed below.

An amorphous poly(lactide) sample (clear, and less than 1 percent crystallinity based on DSC) and a crystalline poly(lactide) sample (opaque, and approximately percent crystallinity based on DSC) were subjected to biodegradation in a compost test (50° C., with aeration). The DSC apparatus was a TA Instruments, Inc., model 910 differential scanning calorimeter with DuPont 9900 computer support system typically programmed to heating at a rate of 10° C. per minute to 200° C. The samples had different optical composition, with the crystalline sample being more than 90 percent poly(L-lactide) and the amorphous sample being less than 80 percent poly(L-lactide) with the balance being either poly(D,L-lactide) or poly(meso-lactide). Samples of each polymer were subjected to a compost test (ASTM D 5338) which included mixing a stabilized compost and providing a source of humidified air while maintaining a temperature of about 50° C. The amorphous sample was completely degraded after 30 days of composting. The crystalline sample was only 23 percent degraded based on carbon dioxide after the same period of time.

Additional samples of these two polymers were subjected to chemical hydrolysis at 50° C. (hydrolysis is believed to be the rate-limiting step in the biodegradation process). The chemical hydrolysis procedure included placing 0.1 gram poly(lactide) in 100 ml of 0.2M phosphate buffer (pH=7.4). The samples were held for 1 week, then filtered, washed with deionized water, and dried at 25° C. under vacuum. The initial weight average molecular weight for each sample was about 70,000. After 1 week the amorphous sample had a weight average molecular weight of 10,000 and the crystalline sample had a weight average molecular weight of 45,000, determined by GPC (the method of Example 7). Neither sample had significant weight loss at this time.

Both of these tests demonstrate that degradation of crystalline poly(lactide) is slower than degradation of amorphous poly(lactide).

EXAMPLE 16

Effect of Monomer Concentration on Film Modulus

Poly(lactide) was precipitated in methanol from a chloroform solution in order to remove the residual lactide monomer. GPC analysis (the method of Example 1) showed the precipitated polymer to contain 0.0 percent lactide.

The polymer was dissolved in chloroform to make a 10 wt percent solution, and lactide was added back to make 5 separate solutions which, after removing the chloroform, are calculated to produce films containing 0.0, 0.2, 0.4, 1.0 and 4.0 weight percent lactide in poly(lactide). These solutions were solvent cast onto glass, dried overnight at room temperature in a fume hood, and removed to a vacuum oven. The films were hung in the vacuum oven and dried at 30° C. for 72 hours. GPC analysis of the vacuum-dried films showed measured lactide levels of 0.0, 0.0, 0.4, 0.7 and 3.7 wt percent.

The films were then tested for film modulus using ASTM procedure D882.

The results are shown below in Table 15.

TABLE 15

| % Lactide | Tensile (psi avg.) | Std. Dev. | % Elongation | Std. Dev. | Elastic Modulus (psi avg.) | Std. Dev. |
|---|---|---|---|---|---|---|
| 0 | 5490 | 636 | 2.85 | 0.14 | 730,000 | 103,000 |
| 0 | 6070 | 123 | 2.85 | 0.22 | 818,000 | 35,000 |
| 0.4 | 5670 | 227 | 2.75 | 0.27 | 779,000 | 44.000 |
| 0.7 | 5690 | 343 | 4.04 | 1.12 | 749,000 | 58,000 |
| 3.7 | 5570 | 458 | 3.33 | 1.43 | 738,000 | 66,000 |

EXAMPLE 17

Rate of Water Uptake Versus Optical Composition

Samples of poly(lactide), made from 80 percent L-lactide and 20 percent of either D,L-lactide or meso-lactide, were ground to pass a 20 mesh screen. The samples were dried and devolatilized under vacuum then removed to a constant humidity chamber maintained at 24° C. and 50 percent relative humidity. The rate of moisture pick-up was determined gravimetrically, with the final results verified by Karl-Fischer water analysis. The rate of moisture pickup is shown below in Table 16.

TABLE 16

| Time | Parts Per Million Weight Gain | |
| --- | --- | --- |
| (Minutes) | L/D,L Polymer | L/Meso Polymer |
| 10 | 600 | 1000 |
| 30 | 1100 | 1500 |
| 60 | 1500 | 1800 |
| 120 | 1600 | 2100 |
| 870 | 2100 | 2600 |
| Final (Karl-Fischer) | 3000 | 2600 |

EXAMPLE 18

Standard Test of Melt Stability

A standard test for determining melt stability is as follows:

A small sample (200 grams or less) of polymer is ground or pelletized and devolatilized by holding under vacuum (about 10 mm Hg) at a temperature of 130° C. or less for 18 hours. At this point the residual lactide content should be 1 wt percent or less. Portions (1–5 grams) of the devolatilized sample are then placed in a 16 ml sample vial, tightly capped, and placed in a 180° C. oil bath. Samples are removed at times of 15 minutes and 1 hour and analyzed for lactide content by GPC or other appropriate techniques. Lactide which may collect on the cooler portions of the vial is included in the product work-up and test.

Melt-stabilized poly(lactide) will show less than percent lactide in the 15 minute sample, and more preferably less than 2 percent lactide in the 1 hour sample. The most highly stabilized poly(lactide)s will maintain lactide contents of less than 1 percent in both the 15 minute and 1 hour samples, preferably less than 0.5 percent. An unstabilized poly (lactide) may reach the equilibrium lactide content at 180° C. of 3.6 wt percent, or may go even higher as lactide is driven from the polymer melt and collects on the cooler top walls of the vial.

EXAMPLE 19

Water Scavenger Experiments

Dried poly(lactide) pellets were processed in a twin screw extruder to devolatilize and to prepare a portion with 0.5 percent by weight of a water scavenger (Stabaxol® P). The strands leaving the extruder are cooled in a water trough and chopped into pellets. Samples of the control and the test sample were then analyzed by the Karl Fischer technique for moisture content, with no drying. The control sample contained 1700 ppm water, the test sample had 450 ppm water. The control sample was then dried under nitrogen at 40° C., reducing the water content to 306 ppm. A vacuum-dried control sample had 700 ppm water.

The as-produced test Sample and the dried control samples were then processed in a ½" single screw extruder (Bradender®) at 160° C., with a retention time of 3 minutes. The number average molecular weight for the dried control sample dropped from an initial value of 44,000 to a final value of 33,000 for the 306 ppm water sample and to 28,000 for the 700 ppm water sample. The test sample number average molecular weight dropped from an initial value of 40,000 to a final value of 33,000.

This sample shows how the water scavenger protected the polymer from moisture pick-up, imparting the same stability as a thorough drying of the control sample. Combining a water scavenger with appropriate drying is expected to give even greater stability.

EXAMPLE 20

Optimization of Catalyst Concentration

A mixture of 80 percent L-lactide and 20 percent D,L-lactide was polymerized using three different levels of tin(II) bis(2-ethyl hexanoate) catalyst. Batches were prepared at initial monomer/catalyst molar ratios of 1000:1, 3000:1, and 20,000:1. Polymerization times were adjusted to reach high conversion without being excessively long and there by causing degradation in the melt. The reaction times were 1,2 and 20 hours, respectively. The polymerization temperature was 180° C. The polymers were ground to a coarse powder and devolatilized at 125° C. and 10 mm Hg overnight. The samples were then reground and 1-gram portions of each were placed into silanized vials, 16 ml capacity. The vials were sealed and placed into an oil bath at 180° C. Vials were then removed at various times and the samples were analyzed by GPC after dissolution in chloroform. The molecular weights and lactide contents are shown below in Table 17.

TABLE 17

| Sample | Time (min) | Number Average Molecular Weight | Weight Average Molecular Weight | Lactide Weight % |
| --- | --- | --- | --- | --- |
| 1000:1 | 0 | 39,000 | 81,300 | 0.8 |
|  | 5 | 28,100 | 57,300 | 2.4 |
|  | 15 | 25,800 | 49,700 | 2.8 |
|  | 30 | 23,100 | 43,800 | 3.7 |
|  | 60 | 22,800 | 43,200 | 3.6 |
| 3000:1 | 0 | 53,100 | 113,600 | 0.6 |
|  | 5 | 39,000 | 76,400 | 0.4 |
|  | 15 | 30,300 | 65,400 | 1.9 |
|  | 30 | 29,000 | 60,400 | 2.7 |
|  | 60 | 28,200 | 55,200 | 2.8 |
| 20000:1 | 0 | 89,200 | 184,000 | 0.0 |
|  | 5 | 81,200 | 165,100 | 0.0 |
|  | 15 | 54,300 | 134,600 | 0.1 |
|  | 30 | 51,100 | 119,600 | 0.0 |
|  | 60 | 49,500 | 111,000 | 0.0 |

These results show the benefit of optimizing the catalyst level used in the polymerization process. Note that both lactide reformation and molecular weight retention benefits are realized from the reduced catalyst levels (higher monomer/catalyst ratio).

It is believed catalyst levels should be limited to 1000:1 for the high end of catalyst usage, with 3000:1 being more preferable and showing somewhat improved stability. Lower levels still, such as 20000:1, show greatly improved stability. Beyond this level it is believed the polymerization rates become too slow to be practical.

EXAMPLE 21

Removal of Tin Catalyst from Poly(lactide) by Precipitation 45 grams of L-lactide and 13 grams of D,L-lactide were charged with 78 milligrams of crystalline lactic acid to a 200 ml round bottom flask. This was heated to 180° C. with magnetic stirring in an oil bath and blanketed with dry nitrogen. Catalyst in the form of tin(II) bis(2-ethyl hexanoate) was added as 0.20 ml of a 0.47 g/ml solution in THF after the molten lactide was at temperature. The mixture was allowed to stir for one minute and then pipetted into 3 silanized glass vials, which were then sealed and placed into a 180° C. oil bath for 75 minutes. The vials were allowed to cool and the polymer recovered by breaking the glass. The polymer was ground to a coarse powder and dissolved in chloroform to make a 10 percent solution. The polymer contained 3.8 percent residual monomer and had a number average molecular weight of 70,000 as determined by GPC measurement (the method of Example 1).

500 ml of methanol were placed in a 1-liter glass blender flask. The blender was turned on to medium speed and 50 ml of the polymer in chloroform solution was poured in over a period of three minutes. After one additional minute of blending the mixture was filtered, then rinsed with 100 ml of methanol, and dried overnight under vacuum. The polymer consisted of a fibrous mat. It contained 0.3 percent residual monomer and had a number average molecular weight of 66,900.

The measured tin level in the precipitated polymer was 337 ppm by weight, compared to a calculated value of 466 ppm for the as-produced polymer. This result indicates the feasibility of reducing residual catalyst levels in lactide polymers by solvent precipitation with the benefit of improved stability as detailed in Example 20.

EXAMPLE 22

Melt-Processability Versus Molecular Weight and Viscosity

The Melt Flow Index (MI) is specified- by ASTM method. D 1238 and is frequently used as a practical measure of viscosity for processing applications. Higher melt flow index corresponds to lower viscosity. Desired values of the melt flow index range from 0.1–2 for a typical extrusion operation, 10–20 for film extrusion or for paper coating, and 1–10 for injection molding.

Based on capillary viscometer measurements the applicants have estimated melt flow index as a function of temperature and molecular weight, with results shown below in Table 18.

TABLE 18

| Number Average Molecular Weight | Weight Average Molecular Weight | Melt Flow Index (Calc) | | |
|---|---|---|---|---|
| | | @ 150° C. | @ 175° C. | @ 200° C. |
| 50,000 | 100,000 | 75 | 1600 | 36000 |
| 75,000 | 150,000 | 18 | 400 | 9000 |
| 100,000 | 200,000 | 6 | 140 | 3000 |
| 150,000 | 300,000 | 1.5 | 34 | 800 |
| 200,000 | 400,000 | 0.6 | 13 | 300 |
| 250,000 | 500,000 | 0.3 | 6 | 120 |
| 300,000 | 600,000 | 0.1 | 3 | 70 |

High temperature processing of poly(lactide) is undesirable because both lactide reformation and molecular weight reductions become more severe as temperature increases. The effect of temperature on degradation is shown, for example, by Jamshidi et al., *Polymer*, vol. 29, pp. 2229–2234 (1988), incorporated herein by reference, and detailed in prior experimental examples. Acceptable temperature ranges vary with the stability of the polymer and the processing temperature.

The table above indicates that for unstabilized polymers, which might be processed at 150° C., an upper limit of 100,000 for the number average molecular weight would be appropriate to achieve a melt flow index near 10 (as might be used for injection molding). For slightly stabilized polymers, which could be processed at 175° C. without degradation or lactide reformation, the number average molecular weight could be as high as 250,000 with a weight average molecular weight of 500,000. For the most stabilized polymers, which could be processed at 200° C. or higher, the molecular weight will be limited only by purity of the lactide. Applications which can operate at lower melt flow indices will have greater tolerance for higher molecular weight.

Note that these processing temperatures are approximations for post-processing, and that the devolatilization operation will frequently be carried out at higher temperatures in order to effectively remove the lactide.

EXAMPLE 23

Anti-Blocking Agents

Two injection molded disks, 2.5 inch diameter, were placed together with a 94 gram weight on top and held at 50° C. for 24 hours. The disks had the following agents compounded therein. The disks were then cooled to room temperature and pulled apart by hand and ranked for blocking characteristics (considerable, slight and none). The following are the results:

TABLE 19

| AGENTS | |
|---|---|
| Poly(lactide) control | considerable |
| 22% wheat gluten | none |
| 10% wheat gluten | slight |
| 22% pecan shell | none |
| 15% pecan shell | slight |
| 23% wollastonite | slight |
| 28% Ultratalc 609 | none |
| 23% Ultratalc 609 | none |
| 28% Microtuff F talc | slight |
| 22% Microtuff F talc | slight |
| 14% Microtuff F talc | slight |
| 2% Microtuff F talc | considerable |

EXAMPLE 24

Coating Examples

Two samples of melt stable poly(lactide) were used in a continuous paper coating trial. The poly(lactide) was dried and devolatilized, with an initial lactide concentration of 0.5 weight percent. The poly(lactide) was produced from lactide using catalyst at a level of 5000:1 molar ratio of monomer to catalyst. The catalyst was tin(II)bis(2-ethyl hexanoate). Stabilizer (Weston PNPG) was added at the start of polymerization at a rate of 0.2 weight percent. The first poly (lactide) sample had an initial weight average molecular weight of 75,000 and the second had an initial weight average molecular weight of 105,000.

The poly(lactide) was melted in a reservoir and then pumped through a die to produce an 8" coating width, using a May Coating Technologies CLS-300 coater and model 50B bulk melter. The die is held in place by pneumatic pressure and floats against the substrate with a melt cushion in between. The substrate was natural kraft paper, basis weight 50 lb, 12" wide.

75,000 molecular weight test: The polymer was melted and pumped at temperatures of 190°–200° C. The pump speed was set to 2.6 lb/min and the line speed was set to 375 feet per minute and 75 feet per minute to give coating thicknesses of approximately 1 mil and 5 mil, respectively. For the 5 mil coating, the temperature at the rewind was 80° C., so a release coated film (MYLAR®) was wound in to eliminate blocking. Subsequent runs incorporated a chill roll and did not use a release film.

105,000 molecular weight test: The polymer was melted and pumped at temperatures of 215°–227° C. At a reservoir temperature of 227° C. the polymer was giving off noticeable fumes. The pump speed was set to 2.6 lb/min and the line speed was set to 375 feet per minute to give a coating thickness of approximately 1 mil. Additional tests were made at line speeds of 150 feet per minute to 500 feet per minute, giving coating thicknesses of 2.5 mil to 0.75 mil, respectively.

The coatings had high gloss and had excellent adhesion to the paper. The coatings exhibited good water repellance, high tear resistance, and increased stiffness.

PLA coated paper (2.5 mils) was tested for blocking at three temperatures 25°, 53°, and 63° C., under a load of 17.5 ounces applied to an area of 262.5 square centimeters, using a substrate placement of film to film, paper to film, film to film (talc dusting). After 24 hours the paper to film and film to film (talc dusting) showed no blocking at 25°, 53° or 63° C. whereas the film to film substrate placement showed no blocking at 25° C. and blocking at 53° C.

EXAMPLE 25

Plasticizer Agents

Dried pellets of devolatilized poly(lactide) were processed in a twin screw extruder to allow compounding of various plasticizing agents. The strands leaving the extruder were cooled in a water trough and chopped into pellets. Samples of the pellets were heated at 20° C./minute to 200° C. in a DSC apparatus, held at 200° C. for 2 minutes and rapidly cooled to quench the samples. The quenched samples were then reheated in the DSC apparatus increasing at 20° C./minute to determine the glass transition temperature. These samples were compared to a polymer with no plasticizer. The effect of the plasticizer on the glass transition temperature is shown in the table below. Glass transition temperatures are taken at the mid-point of the transition.

TABLE 20

| SAMPLE | $T_g$(C.) | Change in $T_g$/wt. Percent additive |
| --- | --- | --- |
| Control | 54.8 | — |
| 8% Dioctyl adipate | 35.0 | 2.5 |
| Control + 40% silica | 54.5 | — |
| Control + 40% silica + 5% dioctyl adipate | 36.0 | 3.7 |
| Control | 54.6 | — |
| 6% Citroflex A-4* | 42.6 | 2.0 |
| 12% Citroflex A-4 | 31.4 | 1.9 |
| Control | 59.3 | — |
| 1.6% Citroflex A-4 | 56.3 | 1.9 |
| 2.9% Citroflex A-4 | 53.1 | 2.1 |
| Control | 58.4 | — |
| 2.1% Citroflex A-4 | 56.1 | 1.1 |
| 3.4% Citroflex A-4 | 50.5 | 2.3 |

*Citroflex is a registered trademark of Morflex, Inc., Greensboro, NC. A-4 is the designation of acetyltri-n-butyl citrate.

These results show the effectiveness of these plasticizers in reducing the glass transition temperature of poly(lactide).

The procedure above was tried using corn oil as a plasticizer. Visual observation showed the corn oil to be not compatible, forming a film on the surface. Corn oil and mineral oil were both not effective as a primary plasticizer with poly(lactide). They may still be useful as a secondary plasticizer, in combination with a compatible primary plasticizer.

It will be understood, however, that even though these numerous characteristics and advantages of the invention have been set forth in the foregoing description, together with details of the structure and function of the invention, the disclosure is illustrative only, and changes may be made in detail, especially in matters of shape, size and arrangement of the parts or in the sequence or the timing of the steps, within the broad principle of the present invention to the full extent indicated by the broad general meaning of the terms in which the appended claims are expressed.

What is claimed:

1. A coated paper product comprising:
   (a) a paper substrate having a first surface; and
   (b) a polymer coating on said paper substrate first surface; said polymer coating comprising a melt stable polymer composition formed from at least: meso-lactide; lactide reactant; and, epoxidized oil;
      (i) said polymer composition having a number average molecular weight of from about 10,000 to about 200,000;
      (ii) said polymer composition having a lactide monomer concentration of less than about 5% by weight; and
      (iii) said lactide reactant being selected from the group consisting of L-lactide, D-lactide and mixtures thereof;
   (c) said polymer composition being formed from a reaction mixture comprising about 3% to about 50% by weight meso-lactide, based on the total weight of meso-lactide and lactide reactant in the reaction mixture; and
   (d) said polymer composition being a polymeric material in a form such that, when isolated and devolatilized, and before incorporation into said polymer coating, it will form less than 1% by weight lactide, upon heating at 180° C. for 1 hour.

2. A coated paper product according to claim 1 wherein:
   (a) said polymer coating comprises a polymer composition having a number average molecular weight of from about 40,000 to about 150,000.

3. A coated paper product according to claim 1 wherein:
   (a) said polymer composition is formed from a reaction mixture including an active hydrogen-bearing compound.

4. A coated paper product according to claim 3 wherein:
   (a) said polymer composition is formed from a reaction mixture including an active hydrogen-bearing compound wherein the active hydrogen-bearing compound is selected from the group consisting of amines, glycols, diols and triols.

5. A coated paper product according to claim 1 wherein:
   (a) said paper substrate is selected from the group consisting of cellulose, lignin, hemicellulose, synthetic fibers and mixtures thereof.

6. A coated paper product according to claim 1 wherein:
   (a) said polymer composition is formed from at least: meso-lactide; lactide reactant; epoxidized oil; and, inorganic filler.

7. A coated paper product according to claim 1 wherein:

(a) said polymer composition is formed from at least: meso-lactide; lactide reactant; epoxidized oil; and, organic filler.

8. A coated paper product according to claim 1 wherein:
(a) said polymer composition is formed from at least: meso-lactide; lactide reactant; epoxidized oil; and, an effective amount of antioxidant.

9. A coated paper product according to claim 1 wherein:
(a) said polymer composition is formed from at least: meso-lactide; lactide reactant; epoxidized oil; and, an effective amount of catalyst deactivating agent.

10. A coated paper product according to claim 1 wherein:
(a) said polymer coating comprises a polymer composition formed from a reaction mixture comprising at least about 7% by weight meso-lactide, based on the total weight of meso-lactide and lactide reactant in the reaction mixture.

11. A coated paper product according to claim 1 wherein:
(a) said paper substrate first surface, with said polymer coating thereon, has a surface energy of at least 35 dynes/cm.

12. A coated paper product according to claim 1 wherein:
(a) said polymer coating includes antistatic agent therein.

13. A coated paper product according to claim 1 wherein:
(a) said polymer coating includes a slip agent therein.

14. A coated paper product according to claim 1 wherein:
(a) said polymer coating includes pigment therein.

15. A coated paper product according to claim 6 wherein:
(a) said filler is compounded into said polymer composition.

16. A coated paper product comprising:
(a) a paper substrate having a first surface; and
(b) a biodegradable polymer coating on said paper substrate first surface; said biodegradable polymer coating comprising a polymer composition comprising the polymer forming reaction product of at least: meso-lactide and L-lactide;
  (i) said polymer composition having a number average molecular weight of 10,000 to 200,000;
  (ii) said polymer composition having a lactide monomer concentration of less than about 5% by weight; and,
  (iii) said polymer composition being formed from a reaction mixture comprising about 3% to about 50% by weight meso-lactide, based on the total weight of meso-lactide, L-lactide and, if present, D-lactide.

17. A coated paper product according to claim 16 wherein:
(a) said polymer composition comprises the polymer-forming reaction product of at least: meso-lactide; L-lactide; and D-lactide.

18. A coated paper product according to claim 16 wherein:
(a) said polymer composition comprises polymer chains including monomer units derived from: meso-lactide; L-lactide and at least one other monomer.

19. A coated paper product according to claim 18 wherein:
(a) said at least one other monomer includes D-lactide.

20. A coated paper product according to claim 16 wherein:
(a) said polymer composition comprises the polymer forming reaction product of: meso-lactide, L-lactide and at least one component capable of reacting into the polymer which is not one of meso-lactide, L-lactide and D-lactide.

21. A coated paper product according to claim 20 wherein:
(a) said at least one component capable of reacting into the polymer which is not one of meso-lactide, L-lactide and D-lactide is material comprising molecules having more than one site for reaction into the polymer.

22. A coated paper product according to claim 20 wherein:
(a) said material comprising molecules having more than one site for reaction into the polymer comprises molecules having at least three sites for reaction into the polymer.

23. A coated paper product according to claim 22 wherein:
(a) said material comprising molecules having at least three sites for reaction into the polymer comprises a triol.

24. A coated paper product according to claim 16 wherein:
(a) said first polymer composition is formed from a mixture including epoxidized oil.

25. A process for preparing coated paper; said process including the steps of:
(a) melt processing a melt stable polymer composition formed from: meso-lactide; lactide reactant; and epoxidized oil, to form a coating composition;
  (i) said polymer composition having a number average molecular weight of 10,000 to 200,000;
  (ii) said polymer composition having a lactide monomer concentration of less than about 5% by weight; and
  (iii) said lactide reactant being selected from the group consisting of L-lactide, D-lactide and mixtures thereof;
  (iv) said polymer composition being formed from a reaction mixture comprising at least 3% by weight meso-lactide, based on the total weight of meso-lactide and lactide reactant; and
(b) applying said coating composition to a paper substrate.

26. A process according to claim 25 including a step of:
(a) calendaring the coated paper.

* * * * *

UNITED STATES PATENT AND TRADEMARK OFFICE
CERTIFICATE OF CORRECTION

PATENT NO. : 5,665,474

DATED : September 9, 1997

INVENTOR(S) : Gruber et al.

It is certified that error appears in the above-identified patent and that said Letters Patent is hereby corrected as shown below:

Col. 12, line 15: "where by" should read --whereby--

Col. 12, line 30: delete "carbon-" after the word "calcium"

Col. 12, line 31: delete "acalcium" before the word "carbonate"

Col. 15, line 27: "glossy" should read --gloss--

Col. 16, line 23, Table 1: "1 32 BETTER" should read --1=BETTER--

Col. 18, line 30, Table 2: "Mv" should read --Mw--

Col. 18, line 30, Table 2: "I Conversion" should read --% Conversion--

Col. 19, line 35, Table 3: "0.34" should read --0.54--

Col. 20, line 5: "(meg/kg*min)" should read --(meq/kg*min)--

Col. 27, line 63: insert --50-- after the word "approximately"

UNITED STATES PATENT AND TRADEMARK OFFICE
CERTIFICATE OF CORRECTION

PATENT NO. : 5,665,474

DATED : September 9, 1997

INVENTOR(S) : Gruber et al.

It is certified that error appears in the above-identified patent and that said Letters Patent is hereby corrected as shown below:

Col. 29, line 38: insert --2-- after the word "than"

Col. 30, line 20: "there by" should read --thereby--

Signed and Sealed this

Thirty-first Day of March, 1998

Attest:

BRUCE LEHMAN

Attesting Officer

Commissioner of Patents and Trademarks